United States Patent
Du et al.

(10) Patent No.: US 12,064,476 B2
(45) Date of Patent: Aug. 20, 2024

(54) ZIKA VIRUS IMMUNOGENIC COMPOSITIONS

(71) Applicants: New York Blood Center, Inc., New York, NY (US); Regents of the University of Minnesota, Minneapolis, MN (US)

(72) Inventors: Lanying Du, Rego Park, NY (US); Wanbo Tai, Elmhurst, NY (US); Fang Li, St. Paul, MN (US)

(73) Assignees: New York Blood Center, Inc., New York, NY (US); Regents of the University of Minnesota, Minneapolis, MN (US)

( * ) Notice: Subject to any disclaimer, the term of this patent is extended or adjusted under 35 U.S.C. 154(b) by 667 days.

(21) Appl. No.: 17/287,938

(22) PCT Filed: Oct. 25, 2019

(86) PCT No.: PCT/US2019/058210
§ 371 (c)(1),
(2) Date: Apr. 22, 2021

(87) PCT Pub. No.: WO2020/087038
PCT Pub. Date: Apr. 30, 2020

(65) Prior Publication Data
US 2021/0308250 A1    Oct. 7, 2021

Related U.S. Application Data

(60) Provisional application No. 62/751,470, filed on Oct. 26, 2018.

(51) Int. Cl.
*A61K 39/12* (2006.01)
*A61K 39/39* (2006.01)
(Continued)

(52) U.S. Cl.
CPC .............. *A61K 39/12* (2013.01); *A61K 39/39* (2013.01); *A61P 31/14* (2018.01); *C12N 7/00* (2013.01); *A61K 2039/55* (2013.01); *C12N 2770/24122* (2013.01); *C12N 2770/24134* (2013.01); *C12N 2770/24171* (2013.01)

(58) Field of Classification Search
None
See application file for complete search history.

(56) References Cited

U.S. PATENT DOCUMENTS

2017/0014502 A1   1/2017   Sumathy et al.
2019/0248875 A1   8/2019   Wu et al.

FOREIGN PATENT DOCUMENTS

WO    2017/212291 A1    12/2017
WO    2018/187799      * 10/2018
(Continued)

OTHER PUBLICATIONS

Deng et al. (Virus Research. 2014; 179: 133-139).*
(Continued)

*Primary Examiner* — Shanon A. Foley
(74) *Attorney, Agent, or Firm* — K&L Gates LLP; Louis C. Cullman; Michelle Glasky Bergman

(57) ABSTRACT

Provided herein are methods of use of subunit immunogenic compositions, in particular for the prevention and treatment of Zika virus infections.

17 Claims, 14 Drawing Sheets
Specification includes a Sequence Listing.

(51) Int. Cl.
*A61P 31/14* (2006.01)
*C12N 7/00* (2006.01)
*A61K 39/00* (2006.01)

(56) References Cited

FOREIGN PATENT DOCUMENTS

WO 2018/187799 A1 10/2018
WO 2020/087038 A1 4/2020

OTHER PUBLICATIONS

Greenspan et al (Nature Biotechnology. 1999; 7: 936-937).*
Yang et al. (Vaccine. 2017; 35: 4287-4294).*
Fowler et al. (Virology. 2023; 579: 101-110).*
Supplementary European Search Report, dated Sep. 27, 2022, for European Patent Application Serial No. 19877365 (search completed Jun. 13, 2022).
Tai et al., Rational design of Zika Virus subunit vaccine with enhanced efficacy. Journal of Virology, vol. 93, No. 17, pp. 1-16 (2019).
Li et al., Evaluating the effect of formulation on the uptake of a Zika subunit vaccine candidate by antigen-presenting cells. Vaccine Technology VII, ECI Symposium Series, Jun. 17, 2018.
International Search Report and Written Opinion, dated Apr. 8, 2020, for International Application Serial No. PCT/US2019/058210 filed on Oct. 25, 2019.
Du et al., Introduction of neutralizing immunogenicity index to the rational design of MERS coronavirus subunit vaccines. Nature Communications, vol. 7, No. 13473, pp. 1-9 (2016).
Tai et al., Critical neutralizing fragment of Zika virus EDIII elicits cross-neutralization and protection against divergent Zika viruses. Emerging Microbes and Infections, vol. 7, No. 7, pp. 1-13 (2018).
Yang et al., Immunization of Zika virus envelope protein domain III induces specific and neutralizing immune responses against Zika virus. Vaccine, Epub 29, vol. 35, No. 33, pp. 4287-4294 (2017).
Barba-Spaeth et al., Structural basis of potent Zika-dengue virus antibody cross-neutralization. Nature, Nature Publishing Group, 536(7614):48-53 (2016).
Stettler et al., Specificity, cross-reactivity, and function of antibodies elicited by Zika virus infection. Science, 353 (6301):823-826 (2016).
Du et al., The latest advancements in Zika virus vaccine development. Expert Review of Vaccines, 16:10, 951-954 (2017).
Abbink et al., Protective efficacy of multiple vaccine platforms against Zika virus challenge in Rhesus monkeys. Science, 353(6304):1129-1132 (2016).
Espinosa et al., Passive transfer of immune sera induced by a Zika virus-like particle vaccine protects AG129 mice against lethal Zika virus challenge. EBioMedicine 27:61-70 (2018).
Dowd et al., Rapid development of a DNA vaccine for Zika virus. Science, 354(6309):237-240 (2016).
Griffin et al., DNA vaccination protects mice against Zika virus-induced damage to the testes. Nature Communications, 8:15743, pp. 1-8 (2017).
Garg et al., Development of virus-like-particle vaccine and reporter assay for Zika virus. Journal of Virology, 91(20):e00834-17 (2017).
To et al., Recombinant Zika virus subunits are immunogenic and efficacious in mice. mSphere, 3(1):e00576-17 (2018).
Sun et al., Treatment of paraquat-induced lung injury with an anti-C5a antibody: Potential clinical application. Crit Care Med, 46:e419-e425 (2018).
Sirohi et al., The 3.8 A resolution cryo-EM structure of Zika virus. Science, 352(6284):467-470 (2016).
Dai et al., Structures of the Zika virus envelope protein and its complex with a flavivirus broadly protective antibody. Cell Host & Microbe, 19:696-704 (2016).
Zhao et al., Structural basis of Zika virus specific antibody protection. Cell, 166(4):1016-1027 (2016).
Modjarrad et al., Safety and immunogenicity of a purified inactivated Zika virus vaccine candidate: preliminary aggregate results from three phase 1a randomized, double-blind, placebo controlled clinical trials. Lancet, 391(10120):563-571 (2018).
Gaudinski et al., Safety, tolerability, and immunogenicity of two Zika virus DNA vaccine candidates in healthy adults: randomised, open-label, phase 1 clinical trials. Lancet, 391(1020):552-562 (2018).
Lazear et al., Zika virus: New clinical syndromes and its emergence in the western hemisphere. Journal of Virology, 90:4864-4875 (2016).
Gatherer et al., Zika virus: a previously slow pandemic spreads rapidly through the Americas. Journal of General Virology, 97:269-273 (2016).
Kassavetis et al., Zika virus-associated Guillain-Barre syndrome variant in Haiti. Neurology, 87:336-337 (2016).
Salinas et al., Zika virus disease-associated Guillain-Barre syndrome-Barranquilla, Colombia 2015-2016. J Neurol Sci, 381:272-277 (2017).
Lucey et al., Congenital Zika syndrome in 2017. JAMA, 317(13):1368-1369 (2017).
Driggers et al., Zika virus infection with prolonged maternal viremia and fetal brain abnormalities. N Engl J Med 374(22):2142-2151 (2016).
Tebas et al., Safety and immunogenicity of an anti-Zika virus DNA vaccine. N Engl J Med, 385(12):e35(1)-e35(10) (2021).
Kostyuchenko et al., Structure of the thermally stable Zika virus. Nature, 533:425-428 (2016).
Jiang et al., Advances in the research and development of therapeutic antibodies against the Zika virus. Cell Mol Immunol, 16:96-97 (2018).
Strafela et al., Zika virus-associated micrencephaly: a thorough description of neuropathologic findings in the fetal central nervous system. Arch Pathol Lab Med, 141:73-81 (2017).
Castro et al., Implications of Zika virus and congenital Zika syndrome for the number of live births in Brazil. PNAS, 115(24):6177-6182 (2018).
Richner et al., Modified mRNA vaccines protect against Zika virus infection. Cell, 168:1114-1125 (2017).
Guo et al., Immunization with a novel human type 5 adenovirus-vectored vaccine expressing the premembrane and envelope proteins of Zika virus provides consistent and sterilizing protection in multiple immunocompetent and immunocompromised animal models. JID, 218:365-377 (2018).
Lopez-Camacho et al., Rational Zika vaccine design via the modulation of antigen membrane anchors in chimpanzee adenoviral vectors. Nat Commun 9:2441 (2018).
Zhang et al., Current advancements and potential strategies in the development of MERS-COV vaccines. Expert Rev. Vaccines, 13(6):761-774 (2014).
Tai et al., Recombinant receptor-binding domains of multiple Middle East respiratory syndrome coronaviruses (MERS-CoVs) induce cross-neutralizing antibodies against divergent human and camel MERS-COVs and antibody escape mutants. Journal of Virology, 91(1):e01651-16 (2017).
Zhang et al., Identification of an ideal adjuvant for receptor-binding domain-based subunit vaccines against Middle East respiratory syndrome coronavirus. Cell Mol Immunol 13:180-190 (2016).
Ma et al., Searching for an ideal vaccine candidate among different MERS coronavirus receptor-binding fragments—The importance of immunofocusing in subunit vaccine design. Vaccine, 32:6170-6176 (2014).
Du et al., A conformation-dependent neutralizing monoclonal antibody specifically targeting receptor-binding domain in Middle East respiratory syndrome coronavirus spike protein. J Virol 88(12):7045-7053 (2014).
Yu et al., A peptide-based viral inactivator inhibits Zika virus infection in pregnant mice and fetuses. Nat Commun 8:15672 (2017).
Tebas et al., ZIKA-001:Safety and immunogenicity of an engineered DNA vaccine against Zika virus infection. N Engl J Med, Author Manuscript (2019).

* cited by examiner

Placenta

FIG. 6B

Fetal brain

FIG. 6C

Placenta

FIG. 6D

Fetal brain

FIG. 6E

FIG. 7A Lung
FIG. 7B Liver
FIG. 7C Heart
FIG. 7D Muscle
FIG. 7E Placenta
FIG. 7F Fetal brain

ZKA64-LALA

ZKA64-LALA

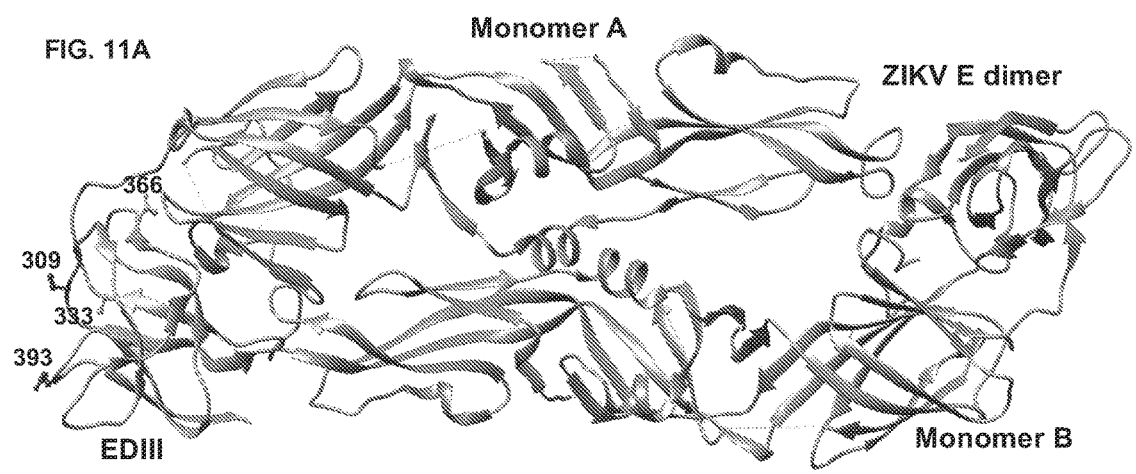
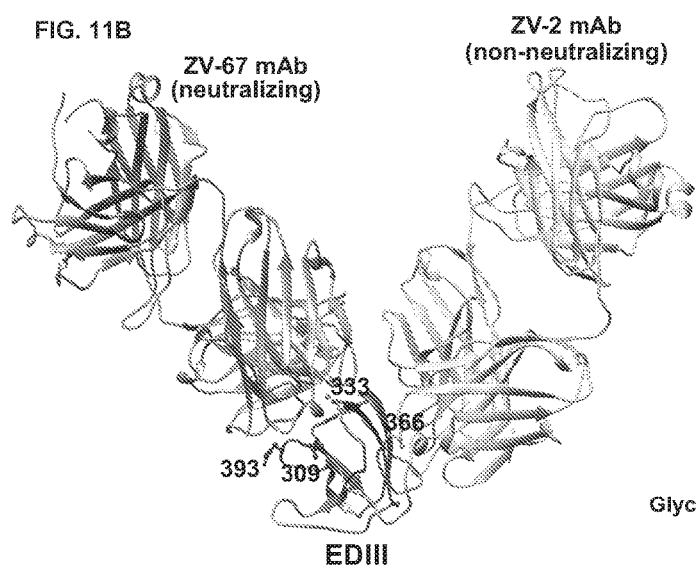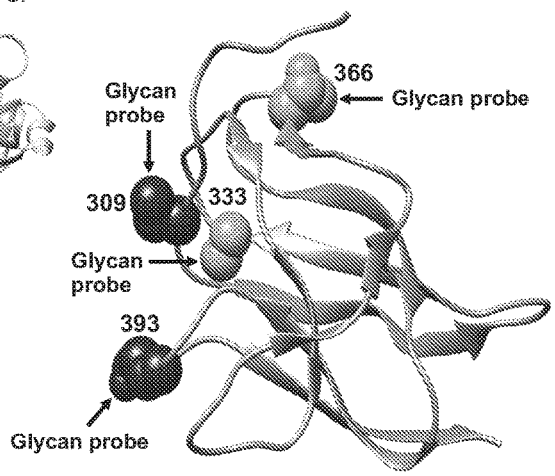

FIG. 12C Sera

FIG. 12D Placenta

FIG. 12E Amniotic fluid

FIG. 12F Fetal brain

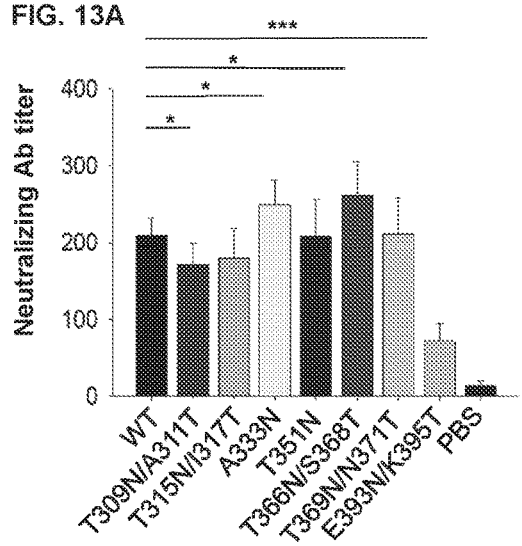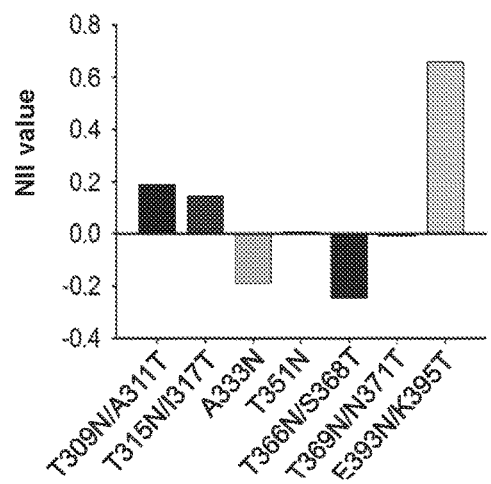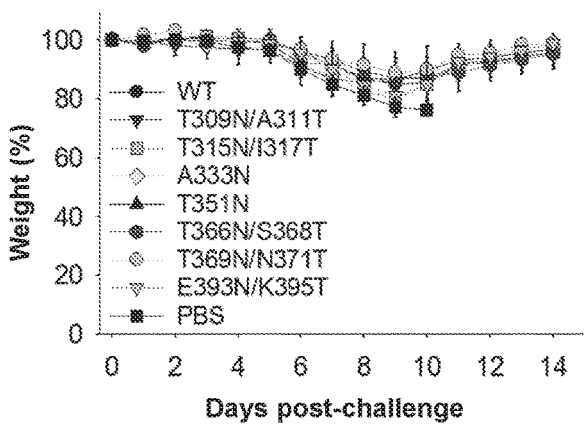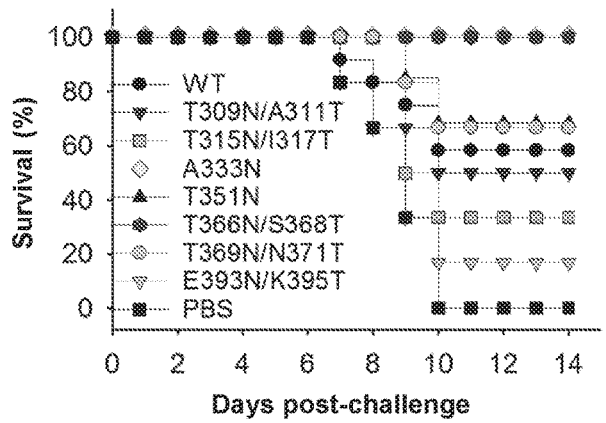

ZIKA VIRUS IMMUNOGENIC COMPOSITIONS

CROSS REFERENCE TO RELATED APPLICATIONS

The present application is a national phase application of International Application PCT/US2019/058210 filed Oct. 25, 2019, which claims the benefit of U.S. Provisional Application No. 62/751,470, filed Oct. 26, 2018, the disclosures of each of which are hereby incorporated by reference in their entirety.

FEDERALLY SPONSORED RESEARCH OR DEVELOPMENT

This invention was made with government support under Grant No. R01AI139092 and R21AI137790 awarded by the National Institutes of Health and Grant No. NYB475, Grant No. NYB486, and Grant No. NYB552 awarded by the New York Blood Center. The government has certain rights in the invention.

TECHNICAL FIELD

The present disclosure relates to methods of use of subunit immunogenic compositions, in particular for use in the prevention and treatment of Zika virus infections.

BACKGROUND

Zika virus (ZIKV) is a flavivirus in the same genus of human pathogenic arboviruses, including dengue virus (DENV), West Nile virus (WNV), yellow fever virus (YFV), and Japanese encephalitis virus (JEV). ZIKV causes neurological diseases such as Guillain-Barre syndrome and congenital Zika syndrome (symptoms include microcephaly, brain abnormalities and other congenital malformations). Despite several ZIKV vaccines currently in clinical trials, no vaccines have been approved for preventing ZIKV infections in humans.

The genome of ZIKV is a single-stranded positive-sense RNA encoding a number of structural and non-structural proteins. The envelope (E) protein, a major structural protein, guides viral entry into host cells by first binding to a host receptor and then fusing viral and host membranes. It forms a viral-envelope-anchored dimer, and each monomer contains multiple structural domains, i.e., domain I (EDI), domain II (EDII), domain III (EDIII), stem region, and transmembrane domain (TM). The E protein is a major inducer of the host immune response and a main target for subunit vaccine design. The individual domains of the E protein may also function in subunit vaccines. Among them, EDI and EDII, but not EDIII, can trigger antibody-enhanced ZIKV entry. Due to its safety, EDIII, which is responsible for binding to host receptor(s), has been our focus for subunit vaccine development. We previously showed that a ZIKV EDIII-based recombinant subunit vaccine is effective in eliciting long-term and broad-spectrum neutralizing antibodies against divergent ZIKV strains. However, its efficacy is not optimal. Improving the efficacy of this subunit vaccine is key to its potential contribution to prevent ZIKV infections.

Despite their general safety, recombinant subunit vaccines often suffer insufficient efficacy. Using Middle East respiratory syndrome (MERS) coronavirus (MERS-COV) as a model system, we have determined that when a recombinant subunit vaccine is made, the previously buried surface areas become artificially exposed and they contain immunodominant non-neutralizing epitopes that distract the host immune system from reacting to neutralizing epitopes. We further developed a neutralizing immunogenicity index (NII) to quantitatively characterize the contribution of each of these epitopes to the overall immunogenicity of the subunit vaccine. In spite of its initial success in MERS-COV subunit vaccine designs, the concepts of the intrinsic limitation of viral subunit vaccines and the NII have not been extended to subunit vaccine designs targeting other viruses.

SUMMARY

Provided herein are methods of use of subunit immunogenic compositions, in particular for use in the prevention and treatment of Zika virus infections.

Disclosed herein are methods for preventing and/or treating a Zika virus infection in a subject in need thereof, the method comprising administering a therapeutically effective amount of an isolated polypeptide comprising an altered structural envelope (E) protein domain III (EDIII), wherein the alteration reduces or prevents the immunogenicity of one or more interfering epitopes of the EDIII. In some embodiments, the method further comprises co-administration of an adjuvant.

In some embodiments, the interfering epitope surrounds residue 333, 366, or 375 of ZIKV EDIII polypeptide. In some embodiments, the alteration comprises creation of a site for N-linked glycosylation. In some embodiments, the N-linked glycosylation site is an NXT or NXS sequence, wherein X is any amino acid. In some embodiments, the alteration comprises at least an N at residue 375 and either a T or S at residue 377. In some embodiments, the alteration comprises at least an N at residue 333 and either a T or S at residue 335. In some embodiments, the alteration comprises at least an N at residue 366 and either a T or S at residue 368. In some embodiments, the alteration comprises M375N/E377T. In some embodiments, the alteration comprises A333N. In some embodiments, the alteration comprises T366N/S368T. In some embodiments, the administration decreases viral titer levels.

In some embodiments of the methods disclosed herein, the administration decreases viral RNA copy number. In some embodiments, the administration increases production of neutralizing antibodies.

In some embodiments of the methods disclosed herein, the adjuvant comprises liposomes, virosomes, saponins, emulsions, or combinations thereof. In some embodiments, the adjuvant comprises aluminum, cholesterol, adjuvant system 04 (AS04), adjuvant system 01E (AS01E), monophosphoryl lipid A (MPL), saponin, oil-in-water, or combinations thereof. In some embodiments, the adjuvant comprises aluminum, MPL, or combinations thereof. In some embodiments, the adjuvant comprises aluminum.

Also disclosed is an immunogenic composition comprising an isolated polypeptide comprising any of SEQ ID NOs 4-6 or 8-22, or a combination thereof. Also disclosed herein is an immunogenic composition comprising an isolated polypeptide consisting of any of SEQ ID NOs 4-6 and 8-22, or a combination thereof. In some embodiments, the immunogenic composition further comprises an adjuvant.

Also disclosed herein are methods for preventing and/or treating a Zika virus infection in a subject in need thereof, the method comprising administering a therapeutically effective amount of an immunogenic composition disclosed herein.

Also disclosed herein are methods for preventing birth defects associated with a Zika virus infection, comprising immunizing a woman who is pregnant, who may become pregnant, or who plans to become pregnant, with an immunogenic composition disclosed herein.

In some embodiments of the methods disclosed herein, the administration increases production of neutralizing antibodies. In some embodiments, the administration decreases viral titer levels. In some embodiments, the administration decreases viral RNA copy number. In some embodiments, as a result of the administration, any pregnancy in the woman does not result in Zika virus-associated birth defects.

Also disclosed herein is the use of an immunogenic composition disclosed herein in the prevention and/or treatment of a Zika virus infection.

Also disclosed herein is the use of an immunogenic composition disclosed herein in the prevention of birth defects associated with Zika virus infection.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A depicts the crystal structure of ZIKV E protein dimer (PDB ID: 5LBV). The two monomeric subunits are shown on top and bottom, respectively. EDIII of monomeric subunit A is shown on left bottom, and residue 375 of EDIII is shown in sticks. FIG. 1B depicts the crystal structures of ZIKV EDIII (shown in the middle) complexed with ZIKV EDIII-specific monoclonal antibodies (mAbs). Neutralizing mAb ZV-67 is shown at bottom (PDB ID: 5KVG), and non-neutralizing mAb ZV-2 is shown on top (PDB ID: 5KVD). FIG. 1C depicts the introduction of an N-linked glycosylation site to residue 375 of ZIKV EDIII (after introducing double mutations M375N/E377T to EDIII).

FIG. 4A-D depicts exemplary antigenicity of the ZIKV EDIII mutant (M375N/E377T) protein vaccine. ELISA was performed to test the binding of mutant M375N/E377T protein to ZIKV EDIII-specific mAbs ZV-2 (FIG. 4A), ZV-54 (FIG. 4B), ZV-67 (FIG. 4C), and ZKA64-LALA (FIG. 4D) mAbs. ZIKV EDIII-WT protein was used as a comparison. The data are presented as means±s.e.m (n=4).

FIG. 5D depicts the calculated neutralizing immunogenicity index (NII) for mutant M375N/E377T protein using serum neutralizing antibody titers ($PRNT_{50}$) from BALB/c, C57BL/6, and $Ifnar1^{-/-}$ mice described above. The NII value was calculated using ($PRNT_{50-WT}$-$PRNT_{50-mutant}$)/$PRNT_{50-WT}$, where $PRNT_{50-WT}$ and $PRNT_{50-mutant}$ represent $PRNT_{50}$ neutralizing antibody titers for WT and mutant (M375N/E377T) EDIII proteins, respectively.

FIG. 6A-E depicts exemplary enhanced efficacy of the ZIKV EDIII mutant (M375N/E377T) protein vaccine in ZIKV-challenged immunocompetent pregnant BALB/c mice and their fetuses. Female BALB/c mice were immunized with WT and mutant (M375N/E377T) EDIII proteins, or PBS control, and mated with male BALB/c mice for pregnancy 10 days post-$2^{nd}$ immunization. The pregnant mice (E10-E13) were challenged with ZIKV (strain R103451, 2×10$^5$ plaque-forming units: PFU), and detected for viral titers and viral RNAs in placenta (FIGS. 6A and 6C) and fetal brain (FIGS. 6B and 6D) by plaque (FIG. 6A-B) and qRT-PCR (FIG. 6C-D) assays 6 days after challenge. The data are presented as means±s.e.m (n=6). Significant differences (***: P<0.001) are shown in each figure. The detection limit for plaque assay was 20 PFU/g, and for qRT-PCR was 2.5×10$^2$ RNA copies/g, of tissue. FIG. 6E depicts the morphology of uteri and embryos in immunized pregnant BALB/c mice 6 days after ZIKV challenge.

FIG. 7A-G depicts exemplary inhibition of ZIKV replication of ZIKV EDIII mutant (M375N/E377T) protein vaccine against ZIKV challenge in pregnant $Ifnar1^{-/-}$ mice and their fetuses. Ifnar1+ mice were immunized with WT and mutant (M375N/E377T) EDIII proteins, or PBS control, and mated with male $Ifnar1^{-/-}$ mice for pregnancy 10 days post-$2^{nd}$ immunization. The pregnant mice (E10-E13) were challenged with ZIKV (strain R103451, 10$^3$ PFU), and viral titers were measured by plaque assay in tissues, including lung (FIG. 7A), liver (FIG. 7B), heart (FIG. 7C), muscle (FIG. 7D), placenta (FIG. 7E), and fetal brain (FIG. 7F) 6 days post-challenge. The data are presented as means+s.e.m (n=6). Significant differences (*: P<0.05; : P<0.01; *: P<0.001) are shown in each figure. The detection limit for lung and heart was 25 PFU/g, and for liver, muscle, placenta, and fetal brain was 20 PFU/g, of tissue. FIG. 7G depicts the morphology of the uteri and embryos of immunized Ifnar1−/− pregnant mice 6 days after ZIKV challenge as described above. Arrows indicate fetal death.

FIG. 8D represents the mean % weight of all surviving mice at the indicated days after challenge, and error bars indicate s.e.m. FIG. 8E depicts serum neutralizing antibody titers of mice before and after challenge with ZIKV (strain R103451) by PRNT assay. The data are presented as mean $PRNT_{50}$+s.e.m (n=4-6). Significant differences (*: P<0.05) are shown in the figure.

FIG. 9A-D depicts exemplary enhanced protective efficacy of passively transferred sera from ZIKV EDIII mutant (M375N/E377T) protein vaccine-immunized mice against ZIKV challenge. Ifnar1−/− mice received passively transferred M375N/E377T-immunized mouse sera, and 6 h later, they were challenged with ZIKV (strain R103451), followed by evaluation of serum viral titers at 3 and 5 days post-challenge, as well as survival and weight changes for 14 days. Mouse sera from ZIKV EDIII-WT- or PBS-immunized mice were included as controls. FIG. 9A depicts ZIKV titers in sera of challenged mice collected at 3 and 5 days after ZIKV challenge (n=5). Significant differences (: P<0.01; *: P<0.001) are shown. Survival (FIG. 9B) and weight (FIG. 9C) of serum transferred mice after ZIKV challenge (n=5-13). Significant difference (*: P<0.05) is shown between the WT and mutant EDIII (M375N/E377T) groups (1:5 dilution). FIG. 9D depicts neutralizing antibodies induced by the above sera transferred into mice against ZIKV (strain R103451) by PRNT assay. Neutralizing activity is expressed as $PRNT_{50}$. The data are presented as means±s.e.m. Significant differences (*: P<0.05) are shown.

FIG. 10A-D depicts exemplary masking of a non-neutralizing epitope on residue 375 of ZIKV EDIII refocused neutralizing immunogenicity on neutralizing epitopes. An ELISA competition assay was performed to test the inhibition of the binding between human neutralizing mAbs ZV-67 or ZKA64-LALA and WT EDIII protein by mutant (M375N/E377T) EDIII-induced mouse sera. Inhibition of the binding between ZV-67 (FIG. 10A, 40C) or ZKA64-LALA (FIG. 10B, 10D) mAb and WT EDIII protein by mutant M375N/E377T-induced sera from BALB/c (FIG. 10A, 10B) and Ifnar1−/− (FIG. 10C, 10D) mice. The EDIII-WT-induced mouse sera were used as a comparison. Mouse sera induced by PBS were used as negative control. The % inhibition in mAb-EDIII binding was calculated in the presence or absence of immunized sera. The data are presented as means±s.e.m. (n=4), and significant differences (***: P<0.001) are shown in each figure.

FIG. 11A-C depicts an exemplary structure-based design of ZIKV EDIII mutant (A333N and T366N/S368T) protein vaccines with enhanced efficacy. FIG. 11A depicts the crystal structure of ZIKV E protein dimer (PDB ID: 5LBV). The two monomeric subunits (monomer A and B) are on top and bottom, respectively. EDIII of monomeric subunit A is shown on left bottom, and the four residues with increased (A333 and T366) or decreased (T309 and E393) immunogenicity are shown in sticks. FIG. 11B depicts the crystal structures of ZIKV EDIII (shown at bottom) complexed with ZIKV EDIII-specific mAbs. Neutralizing mAb ZV-67 (PDB ID: 5KVG) and non-neutralizing mAb ZV-2 (PDB ID: 5KVD) are shown on left and right, respectively. FIG. 11C depicts the introduction of an N-linked glycosylation site at residues T309, A333, T366, and E393 of ZIKV EDIII (after introducing single or double mutations T309N/A311T, A333N, T366N/S368T, and E393N/K395T to EDIII).

FIG. 12A-F depicts exemplary neutralizing antibodies and protection induced by ZIKV EDIII mutant proteins (i.e., T309N/A311T, T315N/1317T, A333N, T351N, T366N/ S368T, T369N/N371T, and E393N/K395T) in immunocompetent BALB/c mice and their fetuses. FIG. 12A depicts improved neutralizing activity of A333N and T366N/S368T ZIKV EDIII mutant proteins in BALB/c mice. Female mice were immunized with ZIKV WT and mutant EDIII proteins, and sera collected at 10 days post-last dose were measured for neutralizing antibodies against ZIKV strain PAN2016 (2016/Panama) by PRNT assay. PBS was used as background control. Neutralizing activity is expressed as $PRNT_{50}$. The data are presented as means±s.e.m (n=5). Significant differences (*: P<0.05; **: P<0.01) are shown. FIG. 12B depicts calculated neutralizing immunogenicity index (NII) for ZIKV EDIII mutant proteins based on serum neutralizing antibody titer ($PRNT_{50}$) using formula $(PRNT_{50\text{-}WT}-PRNT_{50\text{-}mutant})/PRNT_{50\text{-}WT}$, where $PRNT_{50\text{-}WT}$ and $PRNT_{50\text{-}mutant}$ represent $PRNT_{50}$ neutralizing antibody titers for WT and mutant EDIII proteins, respectively. (FIG. 12C-F) Demonstrate enhanced efficacy of A333N and T366N/S368T ZIKV EDIII mutant proteins in protecting pregnant BALB/c mice and their fetuses against high-dose ZIKV (strain PAN2016, $5 \times 10^4$ PFU) challenge. The immunized BALB/c mice were mated with male BALB/c mice and the pregnant mice (E10-E13) were challenged with ZIKV after injection with anti-Ifnar1 antibody, followed by detection of viral titers by plaque assay in sera (FIG. 12C) at 3 days, as well as placenta (FIG. 12D), amniotic fluid (FIG. 12E), and fetal brain (FIG. 12F) at 5 days, post-challenge. Significant differences (*: P<0.05; : P<0.01; *: P<0.001) are shown in FIG. 12C-F, and the data are presented as means±s.e.m (n=5). The detection limit was 25 PFU/ml of sera and amniotic fluid, or 25 PFU/g of tissue (placenta and fetal brain).

FIG. 13A-D depicts exemplary neutralizing antibodies and protection induced by ZIKV EDIII mutant proteins (i.e., T309N/A311T, T315N/1317T, A333N, T351N, T366N/ S368T, T369N/N371T, and E393N/K395T) in immunocompromised Ifnar1-mice. FIG. 13A depictsimproved neutralizing activity of A333N and T366N/S368T ZIKV EDIII mutant proteins in Ifnar1$^{-/-}$ mice. Male and female mice were immunized with ZIKV WT and mutant EDIII proteins, and sera collected at 10 days post last-dose were measured for neutralizing antibodies against ZIKV (strain R103451) by PRNT assay. PBS was used as background control. Neutralizing activity is expressed as $PRNT_{50}$. The data are presented as means±s.e.m (n=6). Significant differences (*: P<0.05; ***: P<0.001) are shown. FIG. 13B depicts the neutralizing immunogenicity index (NII) for ZIKV EDIII mutant proteins based on serum neutralizing antibody titer ($PRNT_{50}$), as calculated above. FIG. 13C-D depict enhanced efficacy of A333N and T366N/S368T ZIKV EDIII mutant proteins in protecting ZIKV-challenged lethal Ifnar1−/− mouse model. The immunized mice were challenged with ZIKV (strain R103451, $10^3$ PFU) 13 days post-last dose to evaluate weight (FIG. 13C) and survival (FIG. 13D) for 14 days (n=6). The % weight in FIG. 13C represents the mean % weight of all survived mice at the indicated days after challenge, and error bars indicate s.e.m.

DETAILED DESCRIPTION

Figure 1A:
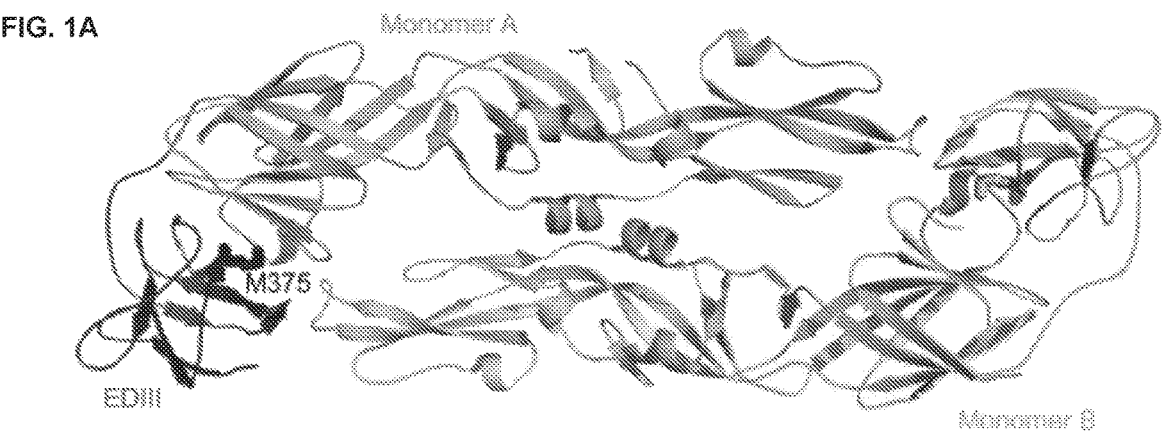
FIG. 1A-C shows an exemplary structure-based design of ZIKV EDIII vaccine with enhanced efficacy.

A number of embodiments of the disclosed subunit immunogenic compositions have been described. Nevertheless, it will be understood that various modifications may be made without departing from the spirit and scope of the present disclosure.

As used herein an "immunogenic composition" refers to an expressed protein, with or without an adjuvant, and which elicits an immune response in the host. The immunogenic compositions disclosed herein are immunoprotective or therapeutic. When the immunogenic compositions may prevent, ameliorate, palliate, or eliminate disease from the host then the immunogenic composition may also optionally be referred to as a vaccine. In some embodiments, the immunogenic composition includes one or more pharmaceutically acceptable excipients and may optionally include an adjuvant.

Zika virus (ZIKV) infection in pregnant women can lead to fetal death and malformations. A previously reported ZIKV envelope protein domain III (EDIII) has been shown as a possible subunit vaccine candidate with cross-neutralization but limited efficacy.

Provided herein are methods of use of subunit immunogenic compositions, such as vaccines, in particular for the prevention and treatment of ZIKV infection. In some embodiments, to improve its efficacy and overcome subunit vaccines' intrinsic limitations, a non-neutralizing epitope on ZIKV EDIII was identified surrounding residue 375 that is buried in the full-length envelope protein but becomes exposed in recombinant EDIII, and this residue was shielded with an engineered glycan probe. Further epitopes with similar properties were identified surrounding residues 333 or 366 of ZIKV EDIII protein. These three epitopes are thus referred to as interfering epitopes.

In various embodiments, EDIII is altered to reduce or prevent the immunogenicity of these three interfering epitopes, so that a higher titer antibody response to neutralizing epitopes is obtained upon immunization with the altered EDIII domains, as compared to that obtained upon immunization with the wild type EDIII. In particular embodiments, this is accomplished by mutating the sequence of the EDIII polypeptide sequence to create a glycosylation site in the vicinity of one or more of these interfering epitopes to obscure, and prevent binding of immunoglobulins to, the peptide epitope. In various embodiments, any one, two, or all three of the interfering epitopes are altered.

Sites for N-linked glycosylation are the amino acid sequences NXT or NXS (and rarely NXC), where X is any naturally encoded amino acid besides proline. In some embodiments, the EDIII polypeptide comprises an N at residue 375 and a T at residue 377, for example, M375N/E377T. In some embodiments, the EDIII polypeptide comprises an N at residue 333 and a T at residue 335, for example A333N/T335T (that is, residue 335 is T in the wild type sequence used in the examples below). In some embodiments, the EDIII polypeptide comprises an N at residue 366 and a T at residue 368, for example, T366N/S368T. In other embodiments, one or more of these T residues are instead S.

In some embodiments, compared to the wild-type EDIII, the mutant EDIII proteins induce significantly stronger neutralizing antibodies in different mouse strains (i.e., BALB/c, C57BL/6, and Ifnar1$^{-/-}$), and also demonstrate significantly improved efficacy in fully protecting mice, particularly pregnant mice and their fetuses, against high-dose lethal ZIKV challenge. In some embodiments, the mutant EDIII immune sera also significantly enhanced the passive protective efficacy in fully protecting mice against lethal ZIKV challenge and the passive protection was positively associated with neutralizing antibody titers. In some embodiments, the enhanced efficacy of the mutant EDIII proteins was due to the shielding of the immunodominant non-neutralizing epitope, which led to immune refocusing on the neutralizing epitopes.

The altered EDIII proteins and fusion proteins are most often produced by recombinant expression in a glycosylation competent expression system, preferably a mammalian expression system, or one in which the glycosylation would not itself be immunogenic in the subjects to be immunized. In alternative embodiments, the EDIII protein is produced by chemical synthesis.

In some embodiments, the altered EDIII polypeptide is produced as a complete protein. In some embodiments, the altered EDIII polypeptide is produced to further comprise a peptide tag, such as a poly-histidine tag. In some embodiments, the altered EDIII polypeptide is produced as a fusion protein. In some embodiments, the EDIII polypeptide is fused to one or more of an Fc domain, hemagglutinin (HA), protein A, foldon, GCN4 trimerization motif, or glutathione S-transferase (GST). Such fusion proteins may also comprise a peptide tag, such as a poly-his tag.

Some embodiments comprise one or more isolated immunogenic polypeptides comprising an altered EDIII polypeptide as described herein. Other embodiments are immunogenic compositions or vaccines comprising one or more such polypeptides. Some embodiments are methods to prevent or treat Zika viral infection by administering such immunogenic polypeptides or compositions, or vaccines, to a person infected with, exposed to, or at risk of exposure to Zika virus. Other embodiments are methods to prevent or reduce the severity of birth defects associated with Zika virus infection by administering, Some embodiments are methods to prevent or treat Zika viral infection by administering such immunogenic polypeptides or compositions, or vaccines, to a woman who is pregnant, who may become pregnant, or who plans to become pregnant. In particular embodiments the isolated immunogenic polypeptide comprising an altered EDIII polypeptide is any one of SEQ ID NOs 4-6 and 8-22.

Some embodiments may be expressed using functional language, for example, means for inducing Zika virus neutralizing epitope-focused immune responses, or means for inducing anti-Zika virus immune responses with reduced reactivity to non-neutralizing (or interfering) epitopes. Examples of such means include SEQ ID NOs 4-6 and 8-22. Similarly, in some embodiments methods of treatment include a step for inducing Zika virus neutralizing epitope-focused immune responses, and the like, corresponding to administration of the herein disclosed immunogenic polypeptides.

TABLE 1

Sequence Identifiers

| SEQ ID NO:1 | ZIKV pre-M and full-length envelope (E) protein (containing amino acids for ZIKV pre-M and Membrane protein (M), and E protein with 505 amino acids) VTRRGSAYYMYLDRNDAGEAISFPTTLGMNKCYIQIMDLGHMCDATMSYECPM LDEGVEPDDVDCWCNTTSTWVVYGTCHHKKGEARRSRRAVTLPSHSTRKLQTR SQTWLESREYTKHLIRVENWIFRNPGFALAAAAIAWLLGSSTSQKVIYLVMIL |
|---|---|

TABLE 1-continued

Sequence Identifiers

LIAPAYSIRCIGVSNRDFVEGMSGGTWVDIVLEHGGCVTVMAQDKPTVDIELV
TTTVSNMAEVRSYCYEASISDMASDSRCPTQGEAYLDKQSDTQYVCKRTLVDR
GWGNGCGLFGKGSLVTCAKFACSKKMTGKSIQPENLEYRIMLSVHGSQHSGMI
VNDTGHETDENRAKVEITPNSPRAEATLGGFGSLGLDCEPRTGLDFSDLYYLT
MNNKHWLVHKEWFHDIPLPWHAGADTGTPHWNNKEALVEFKDAHAKRQTVVVL
GSQEGAVHTALAGALEAEMDGAKGRLSSGHLKCRLKMDKLRLKGVSYSLCTAA
FTFTKIPAETLHGTVTVEVQYAGTDGPCKVPAQMAVDMQTLTPVGRLITANPV
ITESTENSKMMLELDPPFGDSYIVIGVGEKKITHHWHRSGSTIGKAFEATVRG
AKRMAVLGDTAWDFGSVGGALNSLGKGIHQIFGAAFKSLFGGMSWFSQILIGT
LLMWLGLNTKNGSISLMCLALGGVLIFLSTAVSADVGCSV

SEQ ID NO: 2    ZIKV full-length E protein (containing ZIKV full-length E protein with amino acids 1-505)
IRCIGVSNRDFVEGMSGGTWVDIVLEHGGCVTVMAQDKPTVDIELVTTTVSNM
AEVRSYCYEASISDMASDSRCPTQGEAYLDKQSDTQYVCKRTLVDRGWGNGCG
LFGKGSLVTCAKFACSKKMTGKSIQPENLEYRIMLSVHGSQHSGMIVNDTGHE
TDENRAKVEITPNSPRAEATLGGFGSLGLDCEPRTGLDFSDLYYLTMNNKHWL
VHKEWFHDIPLPWHAGADTGTPHWNNKEALVEFKDAHAKRQTVVVLGSQEGAV
HTALAGALEAEMDGAKGRLSSGHLKCRLKMDKLRLKGVSYSLCTAAFTFTKIP
AETLHGTVTVEVQYAGTDGPCKVPAQMAVDMQTLTPVGRLITANPVITESTEN
SKMMLELDPPFGDSYIVIGVGEKKITHHWHRSGSTIGKAFEATVRGAKRMAVL
GDTAWDFGSVGGALNSLGKGIHQIFGAAFKSLFGGMSWFSQILIGTLLMWLGL
NTKNGSISLMCLALGGVLIFLSTAVSAD SEQ ID NO: 3    ZIKV E protein domain III (EDIII) wild-type (WT) (containing ZIKV E protein amino acids 298-409)
LRLKGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHWHRS
GSTIGK SEQ ID NO: 4    ZIKV EDIII M375N/E377T mutant protein (containing ZIKV E protein amino acids 298-409 with M375N and E377T mutations)
LRLKGVSYSLCTAAFTFTKIPAETLHGTVTVEVQYAGTDGPCKVPAQMAVDMQ
TLTPVGRLITANPVITESTENSKMNLTLDPPFGDSYIVIGVGEKKITHHWHRS
GSTIGK SEQ ID NO: 5    ZIKV EDIII WT-Fc protein (containing ZIKV E wild-type protein amino acids 298-409 with human Fc (hFc) sequences)
LRLKGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHWHRS
GSTIGKRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFS
CSVMHEALHNHYTQKSLSLSPGK SEQ ID NO: 6    ZIKV EDIII M375N/E377T-Fc mutant protein (containing ZIKV E wild-type protein amino acids 298-409 with M375N and E377T mutations, and hFc sequences)
LRLKGVSYSLCTAAFTFTKIPAETLHGTVTVEVQYAGTDGPCKVPAQMAVDMQ
TLTPVGRLITANPVITESTENSKMNLTLDPPFGDSYIVIGVGEKKITHHWHRS
GSTIGKRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFS
CSVMHEALHNHYTQKSLSLSPGK SEQ ID NO: 7    ZIKV EDIII WT-His protein (containing ZIKV E wild-type protein amino acids 298-409 and His6)
LRLKGVSYSLCTAAFTFTKIPAETLHGTVTVEVQYAGTDGPCKVPAQMAVDMQ
TLTPVGRLITANPVITESTENSKMMLELDPPFGDSYIVIGVGEKKITHHWHRS
GSTIGKHHHHHH SEQ ID NO: 8    ZIKV EDIII M375N/E377T-His mutant protein (containing ZIKV E wild-type protein amino acids 298-409 with M375N and E377T mutations, and His6)
LRLKGVSYSLCTAAFTFTKIPAETLHGTVTVEVQYAGTDGPCKVPAQMAVDMQ
TLTPVGRLITANPVITESTENSKMNLTLDPPFGDSYIVIGVGEKKITHHWHRS
GSTIGKHHHHHH SEQ ID NO: 9    ZIKV EDIII A333N mutant protein (containing ZIKV E protein amino acids 298-409 with A333N mutation)
LRLKGVSYSLCTAAFTFTKIPAETLHGTVTVEVQYNGTDGPCKVPAQMAVDMQ
TLTPVGRLITANPVITESTENSKMMLELDPPFGDSYIVIGVGEKKITHHWHRS
GSTIGK TABLE 1-continued Sequence Identifiers SEQ ID NO: 10 ZIKV EDIII T366N/S368T mutant protein (containing ZIKV E protein amino acids 298-409 with T366N and S368T mutations)
LRLKGVSYSLCTAAFTFTKIPAETLHGTVTVEVQYAGTDGPCKVPAQMAVDMQ
TLTPVGRLITANPVINETTENSKMMLELDPPFGDSYIVIGVGEKKITHHWHRS
GSTIGK SEQ ID NO: 11 ZIKV EDIII A333N-Fc mutant protein (containing ZIKV E protein amino acids 298-409 with A333N mutation, and hFc sequences)
LRLKGVSYSLCTAAFTFTKIPAETLHGTVTVEVQYNGTDGPCKVPAQMAVDMQ
TLTPVGRLITANPVITESTENSKMMLELDPPFGDSYIVIGVGEKKITHHWHRS
GSTIGKRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFS
CSVMHEALHNHYTQKSLSLSPGK SEQ ID NO: 12 ZIKV EDIII T366N/S368T-Fc mutant protein (containing ZIKV E protein amino acids 298-409 with T366N and S368T mutations, and hFc sequences)
LRLKGVSYSLCTAAFTFTKIPAETLHGTVTVEVQYAGTDGPCKVPAQMAVDMQ
TLTPVGRLITANPVINETTENSKMMLELDPPFGDSYIVIGVGEKKITHHWHRS
GSTIGKRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFS
CSVMHEALHNHYTQKSLSLSPGK SEQ ID NO: 13 ZIKV EDIII T309N/A311T mutant protein (containing ZIKV E protein amino acids 298-409 with T309N and A311T mutations)
LRLKGVSYSLCNATFTFTKIPAETLHGTVTVEVQYAGTDGPCKVPAQMAVDMQ
TLTPVGRLITANPVITESTENSKMMLELDPPFGDSYIVIGVGEKKITHHWHRS
GSTIGK SEQ ID NO: 14 ZIKV EDIII T315N/1317T mutant protein (containing ZIKV E protein amino acids 298-409 with T315N and 1317T mutations)
LRLKGVSYSLCTAAFTFNKTPAETLHGTVTVEVQYAGTDGPCKVPAQMAVDMQ
TLTPVGRLITANPVITESTENSKMMLELDPPFGDSYIVIGVGEKKITHHWHRS
GSTIGK SEQ ID NO: 15 ZIKV EDIII T351N mutant protein (containing ZIKV E protein amino acids 298-409 with T351N mutation)
LRLKGVSYSLCTAAFTFTKIPAETLHGTVTVEVQYAGTDGPCKVPAQMAVDMQ
NLTPVGRLITANPVITESTENSKMMLELDPPFGDSYIVIGVGEKKITHHWHRS
GSTIGK SEQ ID NO: 16 ZIKV EDIII T369N/N371T mutant protein (containing ZIKV E protein amino acids 298-409 with T369N and N371T mutations)
LRLKGVSYSLCTAAFTFTKIPAETLHGTVTVEVQYAGTDGPCKVPAQMAVDMQ
TLTPVGRLITANPVITESNETSKMMLELDPPFGDSYIVIGVGEKKITHHWHRS
GSTIGK SEQ ID NO: 17 ZIKV EDIII E393N/K395T mutant protein (containing ZIKV E protein amino acids 298-409 with E393N and K395T mutations)
LRLKGVSYSLCTAAFTFTKIPAETLHGTVTVEVQYAGTDGPCKVPAQMAVDMQ
TLTPVGRLITANPVITESTENSKMMLELDPPFGDSYIVIGVGNKTIHHWHRS
GSTIGK SEQ ID NO: 18 ZIKV EDIII T309N/A311T-Fc mutant protein (containing ZIKV E protein amino acids 298-409 with T309N and A311T mutations, and hFc sequences)
LRLKGVSYSLCNATFTFTKIPAETLHGTVTVEVQYAGTDGPCKVPAQMAVDMQ
TLTPVGRLITANPVITESTENSKMMLELDPPFGDSYIVIGVGEKKITHHWHRS
GSTIGKRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFS
CSVMHEALHNHYTQKSLSLSPGK SEQ ID NO: 19 ZIKV EDIII T315N/1317T-Fc mutant protein (containing ZIKV E protein amino acids 298-409 with T315N and 1317T mutations, and hFc sequences)
LRLKGVSYSLCTAAFTFNKTPAETLHGTVTVEVQYAGTDGPCKVPAQMAVDMQ TABLE 1-continued Sequence Identifiers

```
            TLTPVGRLITANPVITESTENSKMMLELDPPFGDSYIVIGVGEKKITHHWHRS
            GSTIGKRSDKTHTCPPCPAPELLGGPSVFLFPPKPKDTLMISRTPEVTCVVVD
            VSHEDPEVKFNWYVDGVEVHNAKTKPREEQYNSTYRVVSVLTVLHQDWLNGKE
            YKCKVSNKALPAPIEKTISKAKGQPREPQVYTLPPSREEMTKNQVSLTCLVKG
            FYPSDIAVEWESNGQPENNYKTTPPVLDSDGSFFLYSKLTVDKSRWQQGNVFS
            CSVMHEALHNHYTQKSLSLSPGK

SEQ ID     ZIKV EDIII T351N-Fc mutant protein (containing ZIKV
NO: 20     E protein amino acids 298-409 with T351N mutation,
           and hFc sequences)
            LRLKGVSYSLCTAAFTFTKIPAETLHGTVTVEVQYAGTDGPCKVPAQMAVDMQ
            NLTPVGRLITANPVITESTENSKMMLELDPPFGDSYIVIGVGEKKITHHWHRS
            GSTIGKRSDKTHTCPPCPAPELLGGPSVFLFPPKPKDTLMISRTPEVTCVVVD
            VSHEDPEVKFNWYVDGVEVHNAKTKPREEQYNSTYRVVSVLTVLHQDWLNGKE
            YKCKVSNKALPAPIEKTISKAKGQPREPQVYTLPPSREEMTKNQVSLTCLVKG
            FYPSDIAVEWESNGQPENNYKTTPPVLDSDGSFFLYSKLTVDKSRWQQGNVFS
            CSVMHEALHNHYTQKSLSLSPGK SEQ ID     ZIKV EDIII T369N/N371T-Fc mutant protein (containing
NO: 21     ZIKV E protein amino acids 298-409 with T369N and
           N371T mutations, and hFc sequences)
            LRLKGVSYSLCTAAFTFTKIPAETLHGTVTVEVQYAGTDGPCKVPAQMAVDMQ
            TLTPVGRLITANPVITESNETSKMMLELDPPFGDSYIVIGVGEKKITHHWHRS
            GSTIGKRSDKTHTCPPCPAPELLGGPSVFLFPPKPKDTLMISRTPEVTCVVVD
            VSHEDPEVKFNWYVDGVEVHNAKTKPREEQYNSTYRVVSVLTVLHQDWLNGKE
            YKCKVSNKALPAPIEKTISKAKGQPREPQVYTLPPSREEMTKNQVSLTCLVKG
            FYPSDIAVEWESNGQPENNYKTTPPVLDSDGSFFLYSKLTVDKSRWQQGNVFS
            CSVMHEALHNHYTQKSLSLSPGK SEQ ID     ZIKV EDIII E393N/K395T-Fc mutant protein (containing
NO: 22     ZIKV E protein amino acids 298-409 with E393N and
           K395T mutations, and hFc sequences)
            LRLKGVSYSLCTAAFTFTKIPAETLHGTVTVEVQYAGTDGPCKVPAQMAVDMQ
            TLTPVGRLITANPVITESTENSKMMLELDPPFGDSYIVIGVGNKTITHHWHRS
            GSTIGKRSDKTHTCPPCPAPELLGGPSVFLFPPKPKDTLMISRTPEVTCVVVD
            VSHEDPEVKFNWYVDGVEVHNAKTKPREEQYNSTYRVVSVLTVLHQDWLNGKE
            YKCKVSNKALPAPIEKTISKAKGQPREPQVYTLPPSREEMTKNQVSLTCLVKG
            FYPSDIAVEWESNGQPENNYKTTPPVLDSDGSFFLYSKLTVDKSRWQQGNVFS
            CSVMHEALHNHYTQKSLSLSPGK SEQ ID     Human Fc (hFc) sequence
NO: 23      RSDKTHTCPPCPAPELLGGPSVFLFPPKPKDTLMISRTPEVTCVVVDVSHEDP
            EVKFNWYVDGVEVHNAKTKPREEQYNSTYRVVSVLTVLHQDWLNGKEYKCKVS
            NKALPAPIEKTISKAKGQPREPQVYTLPPSREEMTKNQVSLTCLVKGFYPSDI
            AVEWESNGQPENNYKTTPPVLDSDGSFFLYSKLTVDKSRWQQGNVFSCSVMHE
            ALHNHYTQKSLSLSPGK SEQ ID     Foldon
NO: 24      GYIPEAPRDGQAYVRKDGEWVLLSTFL

SEQ ID     GCN4
NO: 25      MKQIEDKIEEILSKIYHIENEIARIKKLIGEV
```

EXAMPLES

Example 1—Construction, Expression and Immunogenicity of Recombinant ZIKV EDIII Mutant (M375N/E377T) Protein

Materials and Methods

Expression and purification of recombinant proteins. ZIKV EDIII protein containing residues 298-409 (i.e., wild-type, WT) was constructed based on ZIKV E (ZikaSPH2015 strain, GenBank accession number KU321639.1) fused with a C-terminal human IgG1 Fc (human Fc) (SEQ. ID NO:23) tag. Mutant ZIKV EDIII protein containing a glycan probe surrounding residue 375 (i.e., M375N/E377T) was constructed by multi-site mutagenesis kits using the EDIII-WT plasmid as template. The recombinant proteins were expressed in 293T cell culture supernatants, and purified by Protein A affinity chromatography.

Mouse immunization. The purified ZIKV EDIII WT (SEQ ID NO:5) and M375N/E377T (SEQ ID NO:6) mutant proteins were used to immunize mice. The 4-6-week-old female BALB/c and C57BL/6, as well as 3-week-old female Ifnar1−/− mice, were intramuscularly (i.m.) immunized with EDIII WT and mutant (M375N/E377T) proteins (10 µg/mouse), or PBS control, in the presence of aluminum (500 µg/mouse) and monophosphoryl lipid A (MPL) (10 µg/mouse) adjuvant combinations. The immunized mice were boosted once with the same immunogens at 4-week intervals, and sera were collected 10 days after last immunization to test neutralizing antibodies.

Western blot. The purified proteins were analyzed by Western blot. The proteins were separated by 10% Tris-Glycine SDS-PAGE gels, and transferred to nitrocellulose membranes. The transferred blot was blocked with 5% fat-free milk in PBST overnight at 4° C., and sequentially incubated with ZIKV E-protein-immunized mouse sera (1:1000) and horseradish peroxidase (HRP)-conjugated goat anti-mouse IgG (1:5,000) for 1 h at room temperature. The signal was visualized with ECL Western blot substrate buffer and Amersham Hyperfilm.

ELISA. ELISA was used to test the binding between ZIKV EDIII proteins and EDIII-specific mouse mAbs ZV-2 and ZV-54, and human mAbs ZV-67 and ZKA64-LALA. ELISA plates were coated with EDIII WT or M375N/E377T mutant proteins overnight at 4° C. and blocked with 2% fat-free milk in PBST for 2 h at 37° C. After three washes, the plates were sequentially incubated with serially diluted mAbs and HRP-conjugated anti-mouse IgG-Fab antibody (for ZV-2 and ZV-54, 1:5,000) or anti-human IgG-Fab antibody (for ZV-67 and ZKA64-LALA, 1:5,000) for 1 h at 37° C. The reaction was detected by substrate 3,3',5,5'-tetramethylbenzidine and stopped with stop solution (1N $H_2SO_4$). Absorbance at $OD_{450}$ nm was measured.

ZIKV plaque-forming assay and plaque reduction neutralization test (PRNT) assay. ZIKV human strain R103451 (2015/Honduras) was amplified in Vero E6 cells to determine viral titers by a standard plaque-forming assay. Viral titers in the tissues and/or sera from the challenged mice were detected using similar approaches as described above. A PRNT was carried out to measure neutralizing antibody titers in immunized mouse sera or EDIII-specific mAbs. ZIKV (100 PFU) was incubated with serially diluted sera or mAbs for 1.5 h at 37° C., and the antibody-virus mixtures were then added to Vero E6 cells and incubated for 1 h at 37° C. The cells were overlaid with medium (1% carboxymethyl cellulose in DMEM containing 2% FBS), and cultured at 37° ° C. for 4-5 days, followed by staining with 0.5% crystal violet. $PRNT_{50}$ or $ND_{50}$ was calculated as the highest dilution of sera or mAbs leading to complete inhibition of viral infectivity in at least 50% of the wells.

Results

Figure 1B:
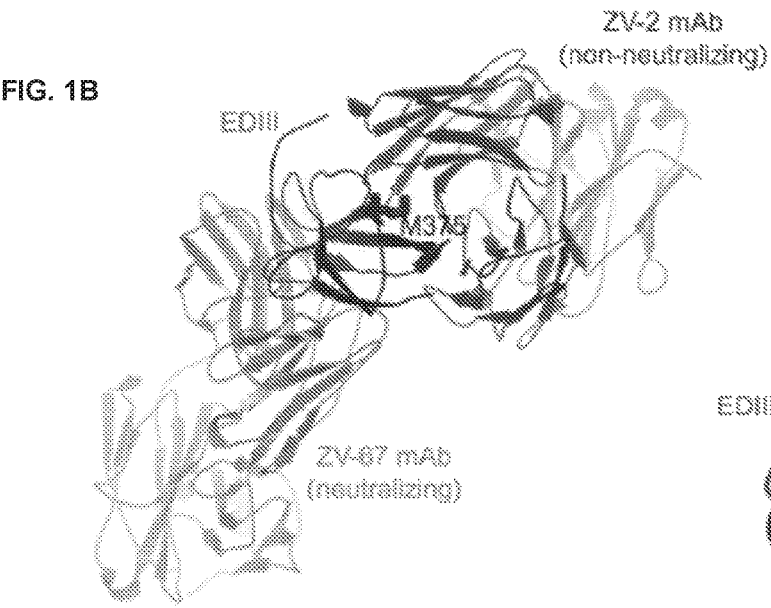
Figure 1C:
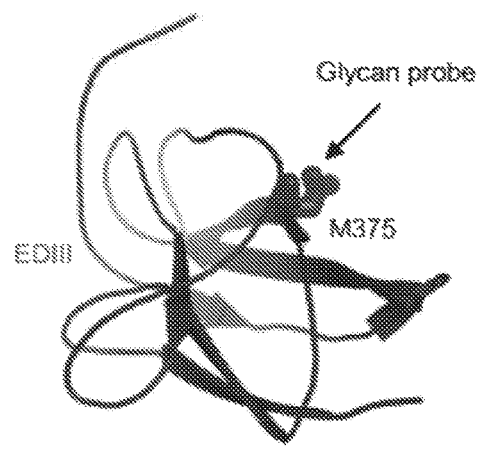
Figure 2:
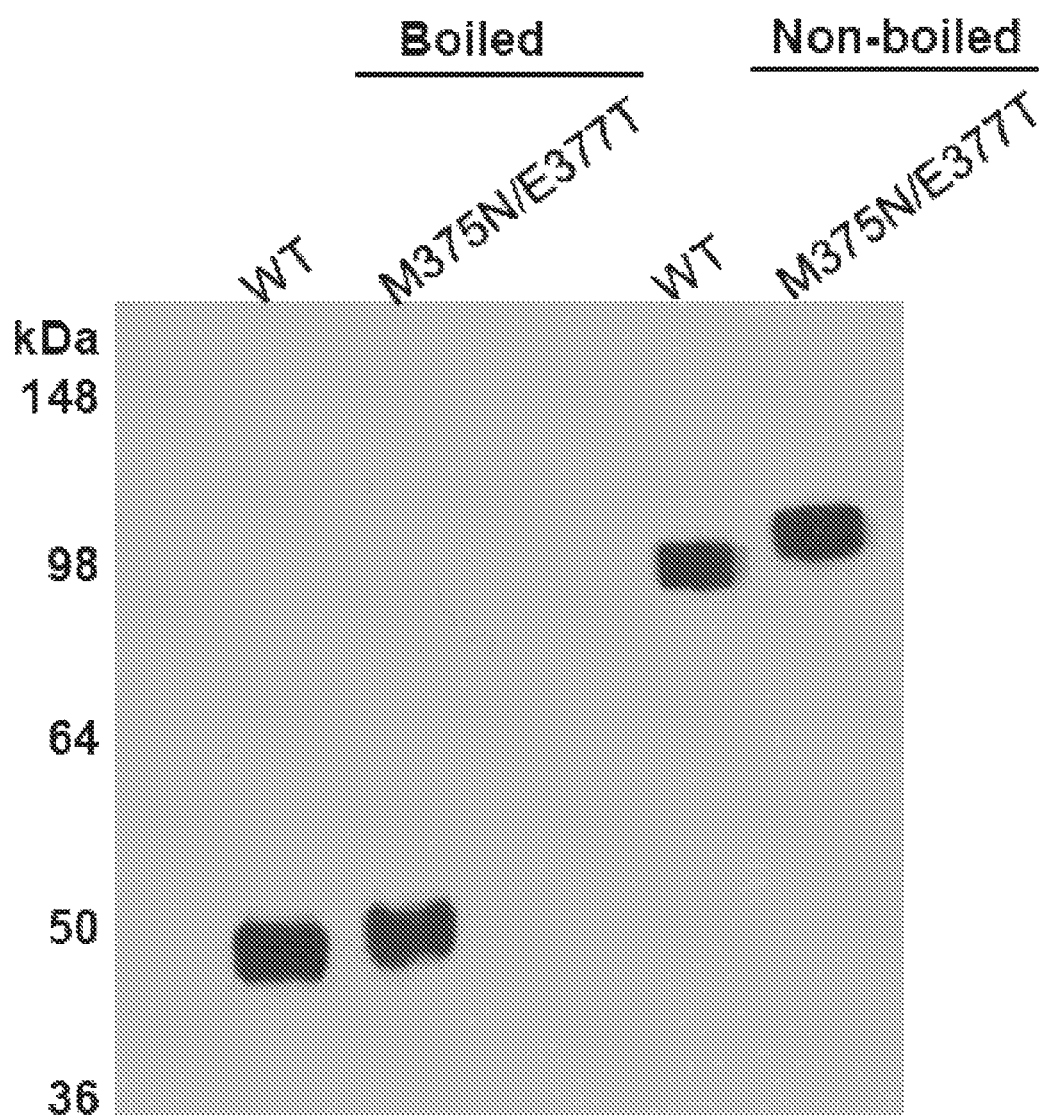
FIG. 2 depicts exemplary Western blot detection of the ZIKV EDIII mutant (M375N/E377T) protein vaccine with residue 375 shielded by a glycan probe. ZIKV wild-type (WT) EDIII was included as a control. Boiled and non-boiled protein samples are shown. The protein molecular weight marker (kDa) is indicated on the left. ZIKV E-specific mouse polyclonal antibody (1:1,000) was used for test.

Identification and Masking of a Non-Neutralizing Epitope on ZIKV EDIII WT Protein To identify an immunodominant non-neutralizing epitope on ZIKV EDIII, we analyzed the crystal structure of ZIKV E protein dimer. We found a patch of surface area on EDIII that is buried in the full-length E protein dimer, but becomes exposed in recombinant EDIII. Met375 is located in the center of this patch and protrudes from a bent B-strand (FIG. 1A-B). Hence, we engineered a glycan probe onto the epitope surrounding residue 375 (i.e., epitope-375) (FIG. 1C). To this end, we introduced double mutations M375N/E377T into EDIII, which changed residue 375 to an N-linked glycosylation site. The ZIKV EDIII mutant (M375N/E377T) protein, along with the EDIII wild-type (WT), was expressed and purified from transfected mammalian 293T cell culture supernatant. Both proteins contain a C-terminal Fc tag and were purified to homogeneity. The result from Western blot showed that both proteins ran as dimers without boiling (due to the Fc dimeric tag and incomplete denaturing), and as monomers after boiling (due to complete denaturing). The EDIII M375N/E377T mutant protein ran slower with a slightly larger molecular weight than the EDIII WT (FIG. 2), indicating that the EDIII mutant was glycosylated after addition of a glycan probe at residue 375.

Figure 3:
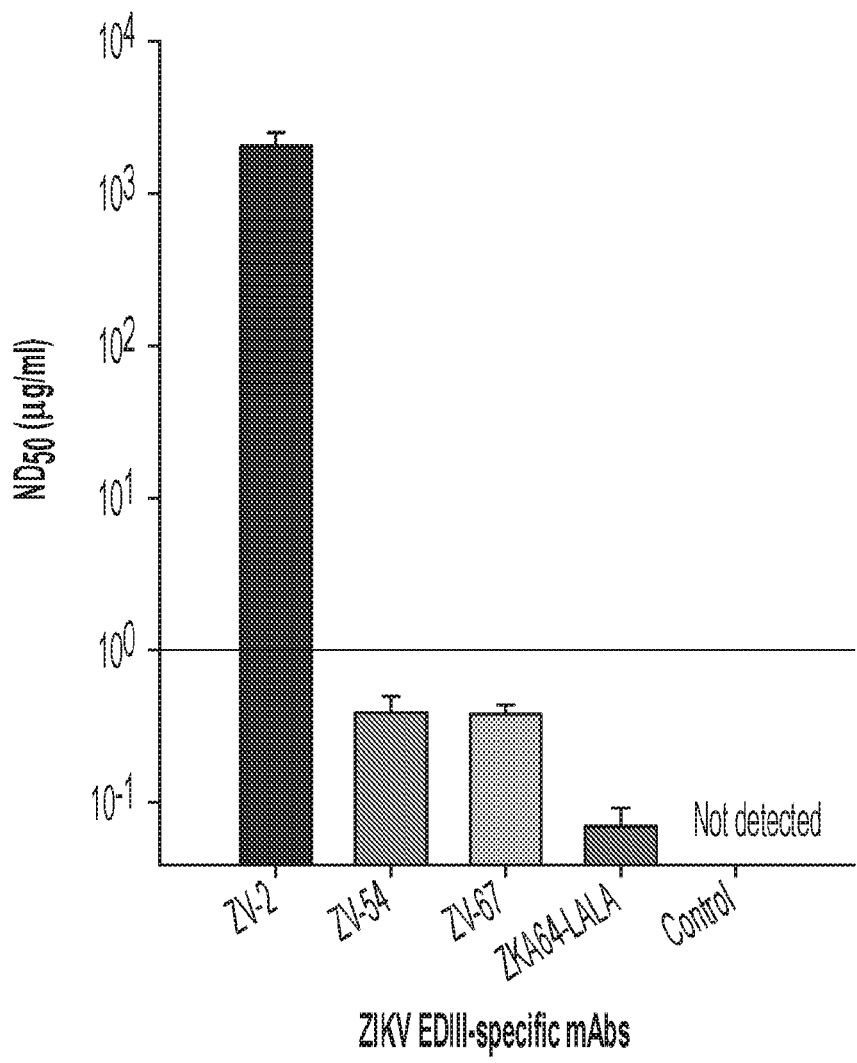
FIG. 3 depicts exemplary neutralizing activity of ZIKV EDIII-specific mAbs against ZIKV infection. Mouse mAbs ZV-2 and ZV-54, as well as human mAbs ZV-67 and ZKA64-LALA, were tested for neutralizing activity against ZIKV strain R103451 (2015/Honduras) by plaque reduction neutralization test (PRNT). PBS was included as control. Neutralizing activity is expressed as mean 50% neutralization dose ($ND_{50}$)±standard error (s.e.m) (n=2).
Figures 4A, 4B, 4C, 4D:
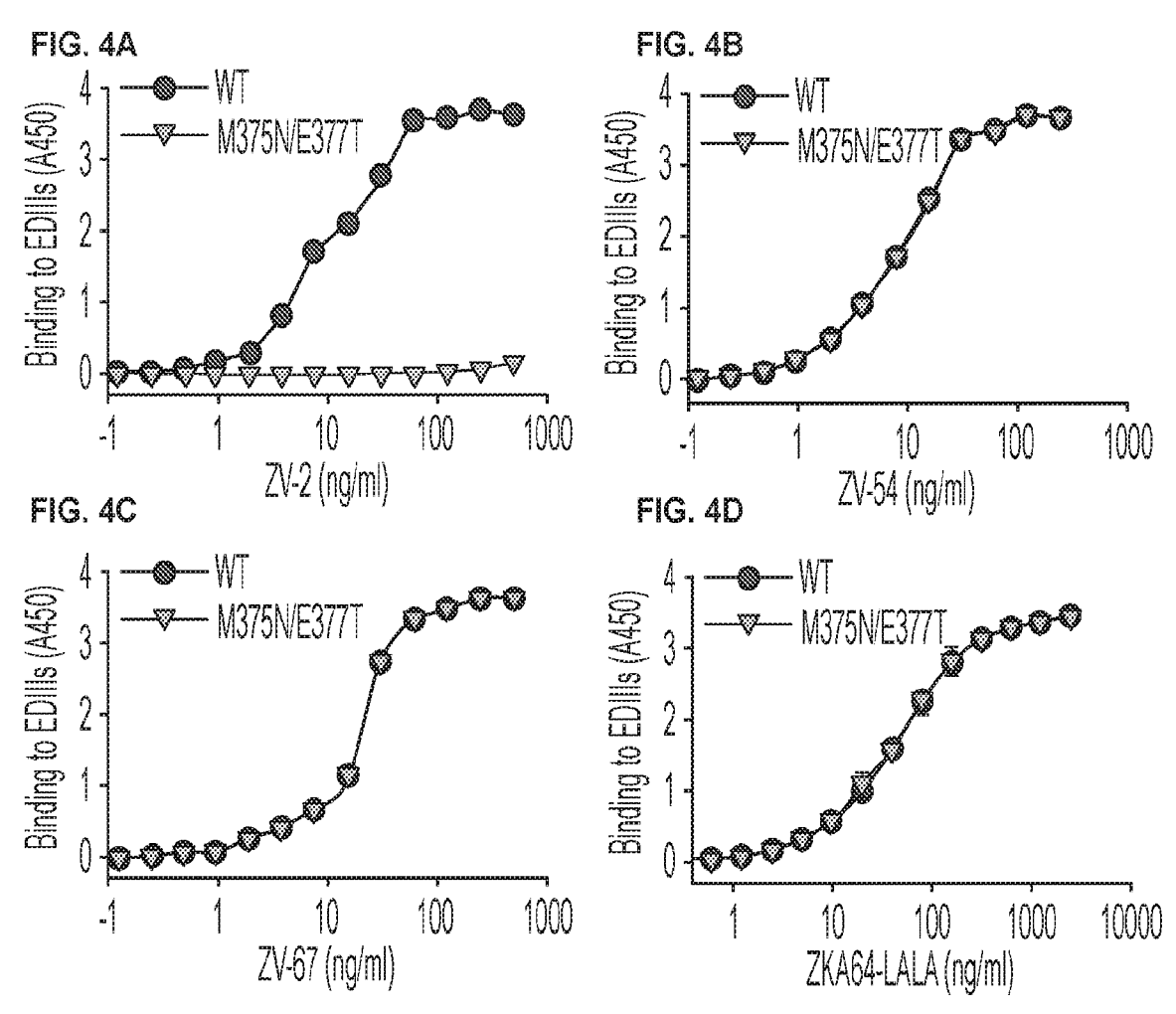

To characterize the conformation of the ZIKV EDIII mutant protein, we investigated the binding interactions between ZIKV EDIII (WT or M375N/E377T mutant) and ZIKV EDIII-specific mAbs using ELISA. Among the mAbs used in this study, ZV-54, ZV-67, and ZKA64-LALA can potently neutralize ZIKV infections in vitro, whereas ZV-2 has no neutralizing activity in vitro in a plaque-based neutralization assay (FIG. 3). The results showed that the ZIKV EDIII mutant (M375N/E377T) protein bound to ZV-54, ZV-67, and ZKA64-LALA neutralizing mAbs, but did not bind to ZV-2. In comparison, the ZIKV EDIII WT protein bound to all of the four mAbs (FIG. 4A-D). We then analyzed the binding sites of these mAbs on EDIII. The crystal structures of ZIKV E protein complexed with ZV-67 and of ZIKV EDIII complexed with ZV-2 revealed that ZV-67 binds to an area that is exposed on the E protein dimer and is likely the receptor-binding site, whereas ZV-2 binds to an area centering epitope-375 that is buried on the E protein dimer but becomes artificially exposed on the recombinant EDIII (FIG. 1B). The structural basis for the binding of ZV-54 and ZKA64-LALA are not known, but these two mAbs may also bind functionally important regions on EDIII and away from epitope-375. Overall, these data further confirm that the ZIKV EDIII mutant (M375N/E377T) protein has successfully incorporated a glycan at residue 375. The data also reveal that despite the introduced glycan, the EDIII mutant (M375N/E377T) protein retains its native structural conformation and antigenicity by binding to at least three different neutralizing mAbs.

Figure 5A:
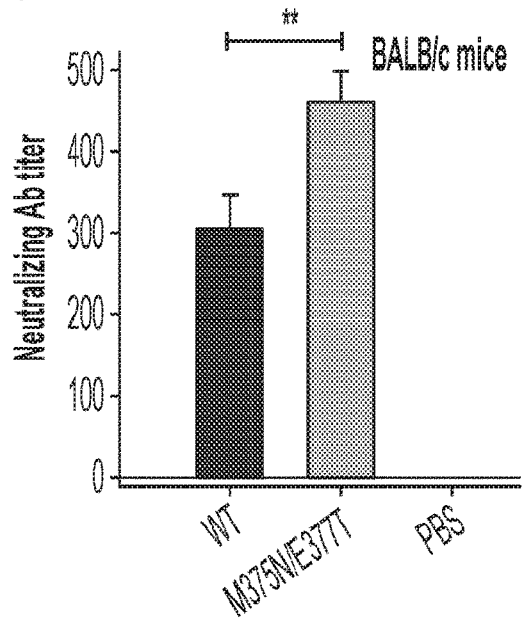
FIG. 5A-D depicts exemplary neutralizing antibodies induced by ZIKV EDIII mutant (M375N/E377T) protein vaccine against ZIKV infection. Immunocompetent BALB/c (FIG. 5A) and C57BL/6 (FIG. 5B) mice, as well as Type-I interferon (i.e., interferon-α/β) receptor (IFNAR)-deficient ($Ifnar1^{-/-}$) mice (C57BL/6 background) (FIG. 5C), were immunized with ZIKV WT and mutant (M375N/E377T) EDIII proteins, and sera were collected at 10 days post $2^{nd}$ immunization to detect neutralizing antibodies against ZIKV (strain R103451) by PRNT assay. PBS was used as background control. Neutralizing activity is expressed as 50% plaque reduction neutralizing antibody titer ($PRNT_{50}$), which was calculated through serum dilutions and neutralizations at 50% plaque reduction using the CalcuSyn computer program. The data are presented as means±s.e.m (n=6). Significant differences (*: P<0.05;*: P<0.01) are shown in FIG. 5A-C.
Figure 5B:
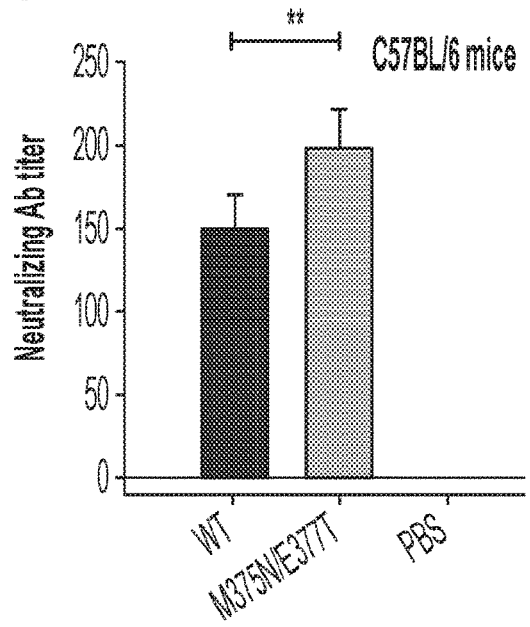
Figure 5C:
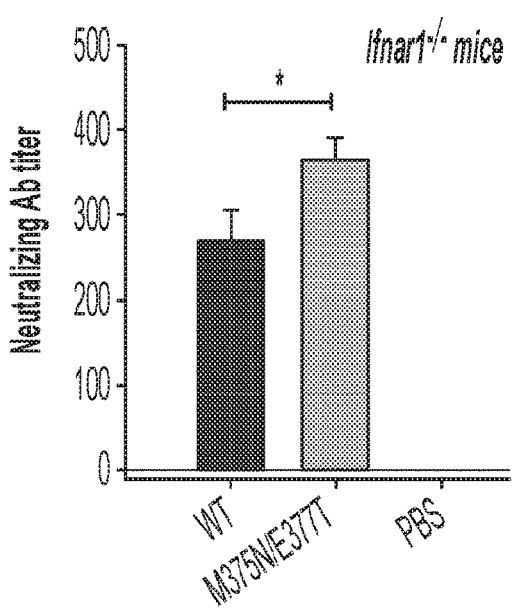
Figure 5D:
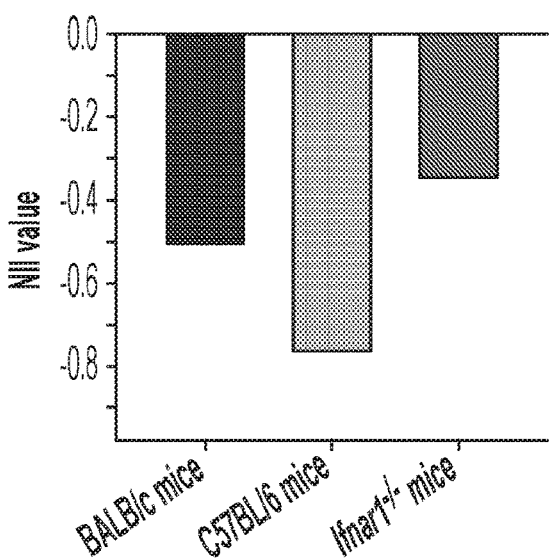

ZIKV EDIII Epitope-375 had Significantly Improved Neutralizing Activity with Negative Neutralizing Immunogenicity Index We previously defined neutralizing immunogenicity index (NII) of an epitope as the contribution of the epitope to the overall neutralizing immunogenicity of the vaccine (Du L. et al., Nat Commun 7:13473, 2016). For epitope-375 on ZIKV EDIII, its NII can be calculated as difference between the neutralizing immunogenicity of the EDIII wild-type (WT) and that of the EDIII mutant (M375N/E377T), divided by the neutralizing immunogenicity of the EDIII WT. To measure the NII of epitope-375 on ZIKV EDIII, we immunized mice with the EDIII WT and mutant (M375N/E377T) proteins individually, and measured the induced serum neutralizing antibody titers. The mice included immunocompetent BALB/c and C57BL/6 mice and immunocompromised Ifnar1−/− mice. The results showed that compared to the EDIII WT, the EDIII mutant (M375N/E377T) protein induced significantly higher titers of anti-ZIKV neutralizing antibodies in all immunized mice (FIG. 5A-C), suggesting that epitope-375 makes negative contribution to the overall neutralizing immunogenicity of ZIKV EDIII vaccine and that masking epitope-375 increases the overall neutralizing immunogenicity of the vaccine. We further calculated the NII of epitope-375 on EDIII. The value of NII varies slightly in different mice: about −0.50 in BALB/c, −0.76 in C57BL/6, and −0.34 in Ifnar1−/− mice (FIG. 5D). The negative sign of NII confirms that the contribution of epitope-375 to the overall neutralizing immunogenicity of the vaccine is negative, and the value of NII suggests that masking epitope-375 increases the overall neutralizing immunogenicity of the vaccine by about 50%, 76%, and 34% (calculated using formula: $(PRNT_{50\text{-}WT}-PRNT_{50\text{-}mutant})/PRNT_{50\text{-}WT}*100$), respectively, in BALB/c, C57BL/6, and Ifnar1−/− mice. Therefore, the measured NII values reveal that epitope-375 is an immunodominant non-neutralizing epitope and that masking it can significantly improve the neutralizing immunogenicity of the ZIKV EDIII vaccine.

Example 2—Protective Efficacy of ZIKV EDIII Mutant (M375N/E377T) Protein Subunit Vaccine in Mouse Models Materials and Methods ZIKV challenge studies and protection evaluation. Ten days after last immunization, female BALB/c and Ifnar1−/− mice immunized with ZIKV EDIII WT (SEQ ID NO:5) and M375N/E377T mutant (SEQ ID NO:6) proteins were mated with respective naïve male mice within the same strains. Mice injected with PBS were included as controls. Pregnant female mice (E10-E13) were intraperitoneally (i.p.) challenged with ZIKV strain R103451 ($10^3$ PFU for Ifnar1−/− mice, and $2 \times 10^5$ PFU for BALB/c mice; 200 µl/mouse). ZIKV viral titers and RNA copies in tissues, placentas and fetal brain collected 6 days post-infection (p.i.) were detected by plaque-forming assay and quantitative reverse transcriptase PCR (qRT-PCR) assay, respectively. In a separate experiment, male Ifnar1−/− mice were (i.p.) challenged with ZIKV (R103451, $10^3$ PFU) 10 days post-last immunization, and evaluated for survival and weight for 14 days p.i. Ten days after completion of the $1^{st}$ challenge experiment, the surviving Ifnar1−/− mice in the EDIII WT and mutant (M375N/E377T) groups were further challenged with high-titer ZIKV (R103451, $5 \times 10^4$ PFU), and observed for survival and weight as described above. Mice with >25% body weight loss were humanely euthanized.

qRT-PCR. ZIKV RNA copies in sera and tissues of challenged mice were detected by qRT-PCR. RNAs were extracted by QIAamp MinElute Virus Spin Kit (for sera) and RNeasy Mini Kit (for tissues), and quantified by one-step qRT-PCR using Power SYBR Green PCR Master Mix, MultiScribe Reverse Transcriptase, and Ambion™ RNase Inhibitor in ViiA 7 Master Cycler PCR System. The forward primers and reverse primers 5'-TTGGTCATGATACTGCT-GATTGC-3' (SEQ ID NO:26) and 5'-CCTTC-CACAAAGTCCCTATTGC-3' (SEQ ID NO:27) were used for the amplification.

Results

Enhanced Efficacy of the ZIKV EDIII Mutant (M375N/E377T) Protein in Protecting Immunized Mice and their Fetuses The efficacy of the ZIKV EDIII mutant (M375N/E377T) protein vaccine in protecting immunocompetent pregnant female mice and their fetuses from ZIKV infection was investigated, as immunocompetent adult mice, such as BALB/c, are non-lethal models for ZIKV infection. To this end, we immunized BALB/c mice with either the ZIKV EDIII wild-type (WT) or mutant (M375N/E377T) protein vaccine, and challenged the pregnant mice (E10-E13) with ZIKV (strain R103451, $2 \times 10^5$ PFU). We then collected placenta and fetal brain 6 days after challenge, and measured the viral titers and RNA copies of ZIKV of these samples using plaque and qRT-PCR assays, respectively. Uteri and embryos were collected simultaneously to observe morphological changes of the uteri and compare fetal status. The results from plaque assay revealed that different from the ZIKV EDIII-WT protein-treated group, viral titers in the placenta and fetal brain of ZIKV EDIII mutant (M375N/E377T) protein-immunized pregnant mice were undetectable (FIG. 6A-B). Similarly, the results from qRT-PCR assay demonstrated that the viral RNA copies in the placenta and fetal brain of the ZIKV EDIII mutant (M375N/E377T) protein-immunized pregnant mice were also undetectable (FIG. 6C-D). As a negative control, the tissues of PBS-treated pregnant mice contained significantly higher viral titers and RNA copies (FIG. 6A-D). In addition, there were no significant morphological changes of the uteri of ZIKV EDIII-WT and mutant (M375N/E377T) protein-immunized pregnant mice and all embryos from these mice were in good conditions, whereas the embryos from the PBS-treated mice were invisible, showing severe resorption in their uteri (FIG. 6E). Collectively, compared to the ZIKV EDIII WT protein, the EDIII mutant (M375N/E377T) protein vaccine protects immunocompetent pregnant mice more effectively from ZIKV infection as evidenced by undetectable viral titers and RNA copies, although both the EDIII WT and mutant vaccines protected the fetuses of immunocompetent pregnant mice from ZIKV infection.

Figure 7G:
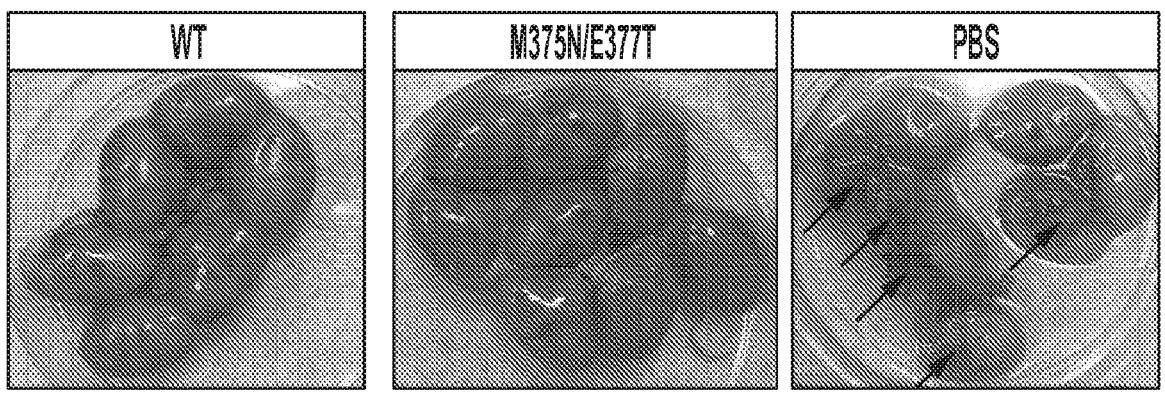

Next, the efficacy of the ZIKV EDIII mutant (M375N/E377T) protein vaccine in protecting immunocompromised Ifnar1−/− mice and their fetuses from ZIKV infection was evaluated, as these mice are lethal models for ZIKV infection. To this end, we immunized female Ifnar1−/− mice and male Ifnar1$^{-/-}$ mice with either the ZIKV EDIII WT or mutant (M375N/E377T) vaccine, and then treated female and male mice differently. First, the immunized male and female mice were mated and pregnant female Ifnar1/mice were challenged with ZIKV (strain R103451, $10^3$ PFU), the tissues were collected (including placenta and fetal brain) 6 days post-challenge, ZIKV titers were measured in these tissues using plaque assay. We also examined the uteri and embryos of these mice 6 days post-challenge. The results showed that compared to the ZIKV EDIII-WT protein-treated group, the viral titers in the ZIKV EDIII mutant (M375N/E377T) protein-immunized female Ifnar1$^{-/-}$ pregnant mice were significantly lower in lung (FIG. 7A), liver (FIG. 7B), heart (FIG. 7C), muscle (FIG. D), and placenta (FIG. 7E), or undetectable in fetal brain (FIG. 7F). Moreover, there were no significant morphological changes of the uteri and all fetuses were in good conditions in ZIKV EDIII WT- and mutant (M375N/E377T) protein-treated mice (FIG. 7G). In the negative control group (i.e., PBS-treated female pregnant Ifnar1$^{-/-}$ mice), the viral titers were very high in all the tested tissues and fetal brain, resulting in significant morphological changes of the uteri with severe resorption or fetal death (FIG. 7A-G).

Figure 8A:
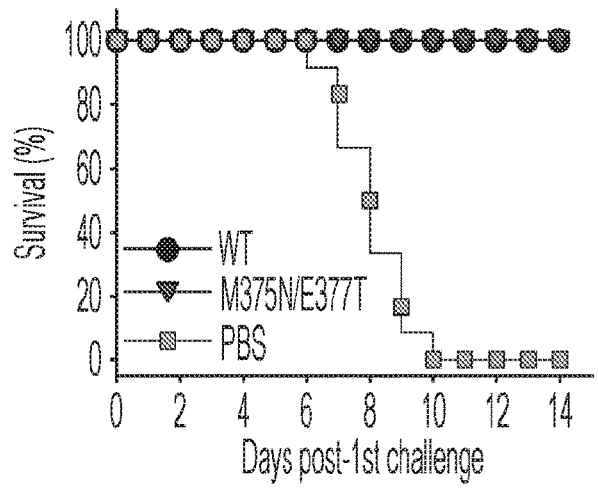
FIG. 8A-E depicts exemplary enhanced protective efficacy of ZIKV EDIII mutant (M375N/E377T) protein vaccine in ZIKV-challenged lethal Ifnar1−/− mouse model. Adult male Ifnar1−/− mice were immunized with ZIKV WT and mutant (M375N/E377T) EDIII proteins, or PBS control, and challenged with ZIKV (R103451, 10$^3$ PFU) 10 days post-2nd immunization to evaluate survival (FIG. 8A) and weight (FIG. 8B) for 14 days (n=6). The surviving Ifnar1−/− mice in the WT and mutant M375N/E377T groups were further challenged with ZIKV (R103451, 5×10$^4$ PFU), and observed for survival (FIG. 8C) and weight (FIG. 8D) as above (n=6). The % weight in FIG. 8B
Figure 8B:
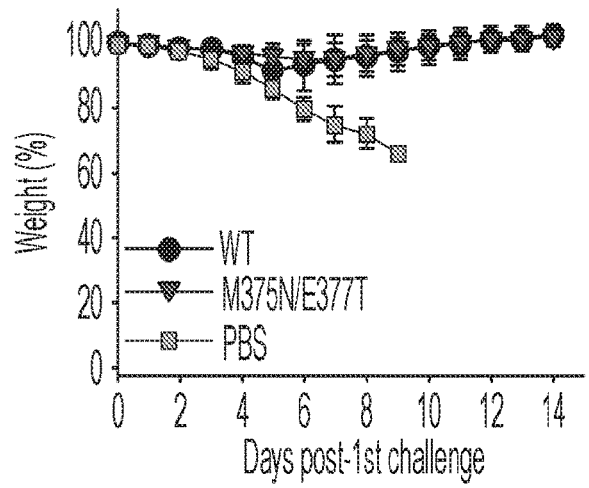
Figure 8C:
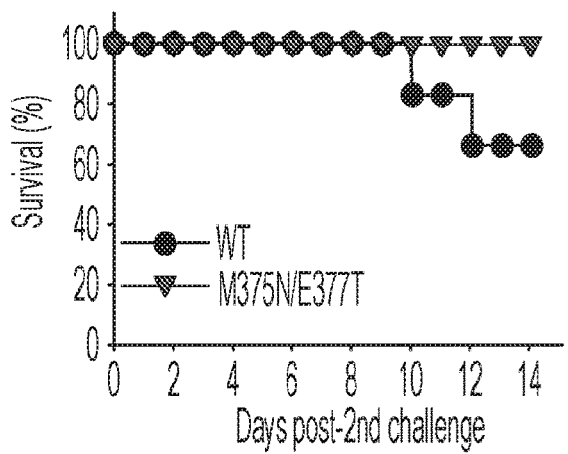
Figure 8D:
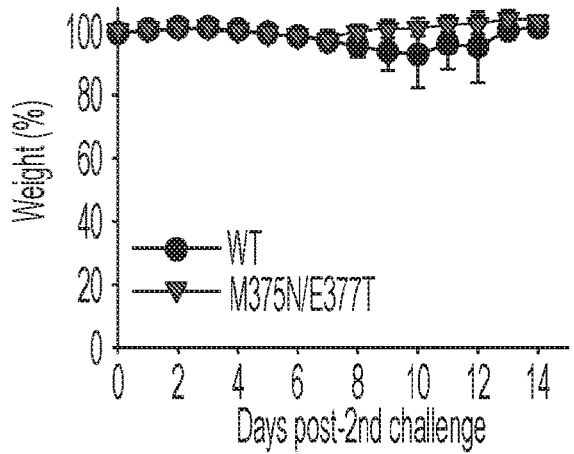
Figure 8E:
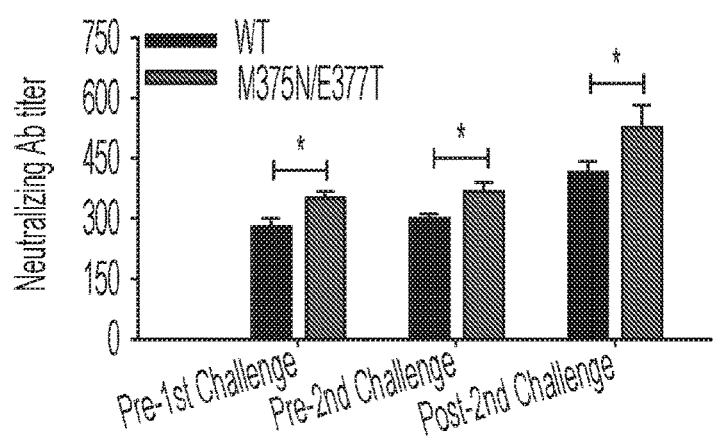

Second, we challenged adult male Ifnar1−/− mice sequentially with ZIKV at low (R103451, $10^3$ PFU) and high (R103451, $5 \times 10^4$ PFU) doses, and observed them for survival and weight changes. The results showed that the male Ifnar1−/− mice immunized with either the ZIKV EDIII WT or the mutant (M375N/E377T) protein vaccine and then challenged with $10^3$ PFU of ZIKV (strain R103451) all survived at 14 days post 1st challenge (FIG. 8A); their weight decreased slightly during days 4-7 post-infection but kept increasing steadily afterwards (FIG. 8B). In contrast, in the negative control group (i.e., PBS-treated mice), all mice showed ≥25% weight loss and were humanely euthanized at day 10 post-infection. All of the surviving mice immunized with either the ZIKV EDIII WT or mutant (M375N/E377T) vaccine were further challenged with a high dose of ZIKV (strain R103451, $5 \times 10^4$ PFU) to investigate whether they can survive lethal high-dose ZIKV infection. The results showed that the EDIII mutant (M375N/E377T)-immunized mice all survived the second, high-dose ZIKV challenge (100% survival) (FIG. 8C), with no obvious weight loss (FIG. 8D). In contrast, only 67% of the EDIII-WT-immunized mice survived the second, high-dose ZIKV challenge, with considerable weight loss during days 7-12 after ZIKV challenge (FIG. 8C-D). Comparison of the serum neutralizing antibodies in the mice before and after ZIKV challenge demonstrated that anti-ZIKV neutralizing antibody titers were significantly higher in the EDIII mutant (M375N/E377T)-immunized mice than in the EDIII-WT-immunized mice before the $1^{st}$- and $2^{nd}$-challenge, particularly after the 2nd-challenge (FIG. 8E). Therefore, the enhanced efficacy of the mutant (M375N/E377T) protein against the high-dose ZIKV infection might be due to the higher serum neutralizing antibodies it induced. Overall, these data demonstrate that compared to the EDIII WT, the EDIII mutant (M375N/E377T) vaccine protects immunocompromised female pregnant mice and their fetuses more effectively from ZIKV infection, as evidenced by significantly reduced or undetectable viral titers, and it also protects immunocompromised adult male mice from high-dose ZIKV infection more effectively, as evidenced by improved survival rate and steadily maintained weight.

Example 3—Passive Protective Efficacy of the ZIKV EDIII Mutant (M375N/E377T) Protein Subunit Vaccine in ZIKV-Susceptible Lethal Mouse Model Materials and Methods Passive protection of ZIKV EDIII mutant (M375N/E377T)-immunized mouse sera against ZIKV challenge in lethal Ifnar1−/− mouse model. The 5-6-week-old male and female Ifnar1$^{-/-}$ mice (n=5-13) were injected (i.p.) with sera (200 µl/mouse: normalized for equal ZIKV EDIII-specific IgG titers at 105, or 1:5 dilution in PBS) of mice immunized with ZIKV EDIII WT (SEQ ID NO:5) or M375N/E377T mutant (SEQ ID NO:6) proteins. Six hours later, mice were i.p. challenged with ZIKV (strain R103451, $10^3$ PFU). Mice injected with PBS-induced Ifnar1$^{-/-}$ mouse sera were included as controls. Neutralizing activity of passively transferred mouse sera was detected by PRNT assay. ZIKV titers were detected from sera collected at 3 days and 5 days post-infection (p.i.) by ZIKV plaque-forming assay. Mouse survival and weight were recorded for 14 days p.i.

Results

Figures 9A, 9B, 9C, 9D:
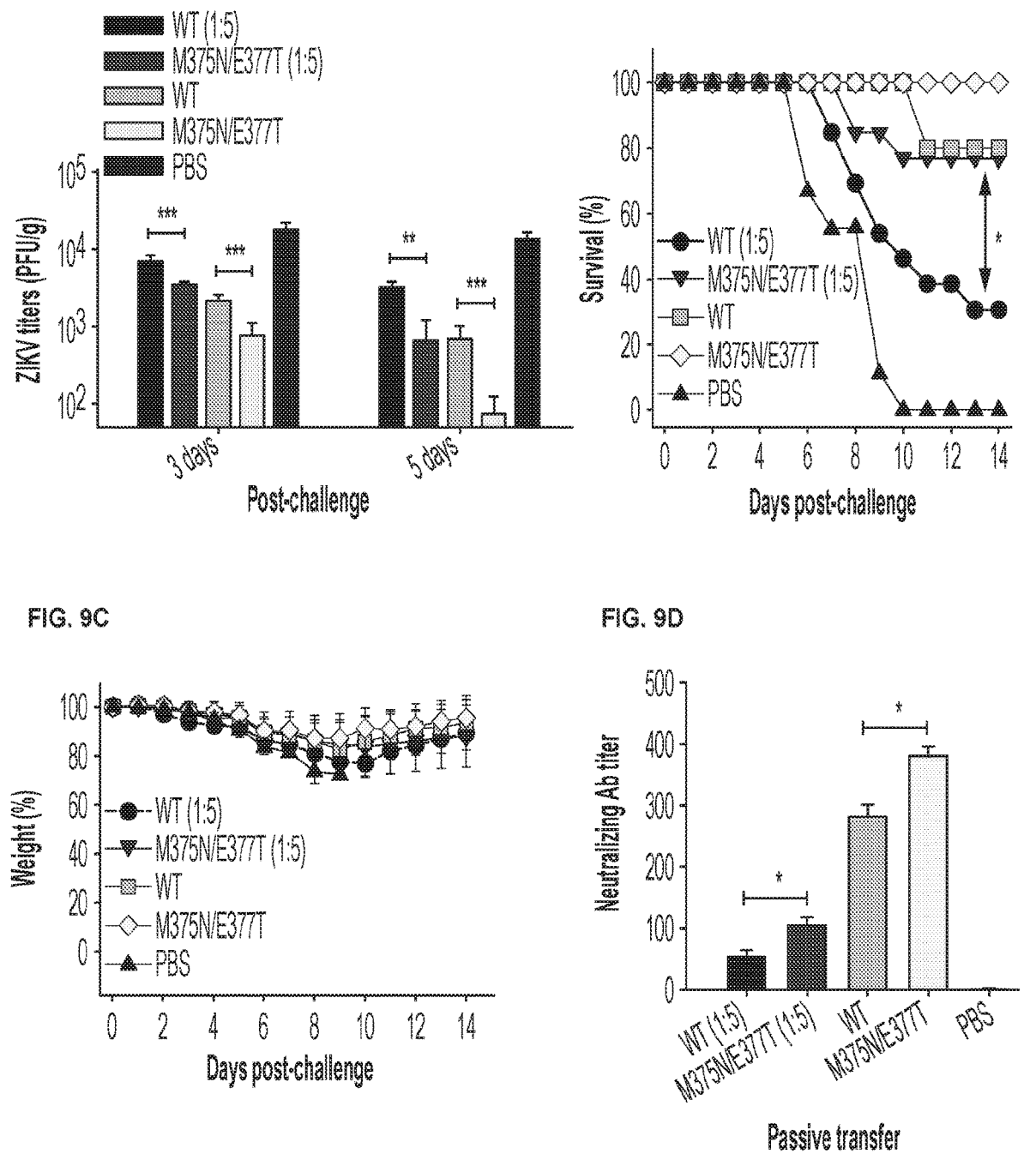

Enhanced Passive Protection of the ZIKV EDIII Mutant (M375N/E377T) Protein-Immunized Mouse Sera in Protecting Lethal Ifnar1−/− Mouse Model Against ZIKV Challenge To further elucidate the enhanced protective efficacy of the ZIKV EDIII mutant (M375N/E377T) protein vaccine and investigate the association between protection and neutralizing antibodies, passive protection was performed using the sera of mice immunized with ZIKV EDIII WT and mutant (M375N/E377T) proteins. As such, sera were pooled from each vaccination group, and normalized for equal ZIKV EDIII-specific IgG titers. Adult Ifnar1−/− mice received passively transferred pooled sera (with or without 1:5 dilution), and challenged with ZIKV as described above, followed by comparison of their viremia, survival rate, and weight changes after ZIKV challenge. The results showed that ZIKV viremia in the mice receiving passively transferred EDIII mutant (M375N/E377T)-immunized sera was significantly lower than in the mice receiving passively transferred EDIII-WT-immunized sera at both 3 and 5 days post-challenge (FIG. 9A). In addition, while about 77% of the mice receiving the diluted EDIII mutant (M375N/E377T)-immunized sera survived the ZIKV challenge, all mice receiving the undiluted sera survived the ZIKV challenge, showing slight weight loss (FIG. 9B-C). In contrast, only about 31% and 80% of the mice survived the ZIKV challenge after receiving EDIII-WT-immunized sera with or without dilution at 1:5, respectively, while the former had significant weight loss during days 8-10 after ZIKV challenge (FIG. 9B-C). Moreover, the EDIII-mutant (M375N/E377T)-immunized sera (with or without 1:5 dilution) had significantly higher-titer anti-ZIKV neutralizing antibodies than the EDIII-WT-immunized sera (with or without 1:5 dilution) (FIG. 9D). As expected, mice transferred with the PBS-injected sera, which showed no anti-ZIKV neutralizing antibodies, had the highest viral titers and weight loss, and 0% survival rate at day 10 post-challenge (FIG. 9B-D). The above data indicate that compared to the ZIKV-EDIII-WT-immunized sera, the EDIII-mutant (M375N/E377T)-immunized sera contained significantly high-titer neutralizing antibodies, thus resulting in the enhanced passive protection against ZIKV challenge, suggesting their positive association.

Example 4—Molecular Mechanism for the Enhanced Efficacy of the ZIKV EDIII Mutant (M375N/E377T) Protein Subunit Vaccine Materials and Methods The competition between ZIKV EDIII-specific human mAbs ZV-67 or ZKA64-LALA and EDIII mutant (M375N/E377T) protein-induced mouse sera for the binding of ZIKV EDIII wild-type (WT) protein was performed using ELISA as described above, except that the binding between EDIII WT and ZV-67 or ZKA64-LALA was tested in the presence of serially diluted mouse sera induced by EDIII WT (SEQ ID NO:5) and M375N/E377T mutant (SEQ ID NO:6) proteins, or PBS, respectively. The binding between EDIII and mAbs was measured by addition of HRP-conjugated anti-human IgG-Fab antibody (1:5,000) and subsequent enzymatic reaction as described above.

Results

Molecular Mechanism for the Enhanced Efficacy of the ZIKV EDIII Mutant (M375N/E377T) Protein Subunit Vaccine To explore the molecular mechanism for the enhanced efficacy of the ZIKV EDIII mutant (M375N/E377T) protein vaccine, we investigated the binding interactions between the ZIKV EDIII wild-type (WT) and EDIII-specific human neutralizing mAbs in the presence of the ZIKV EDIII mutant (M375N/E377T) protein-induced mouse sera using ELISA. The EDIII-WT-induced mouse sera were used as a comparison. The result showed that compared to the EDIII-WT-induced mouse sera, the EDIII mutant (M375N/E377T)-induced sera from both immunocompetent BALB/c mice (FIG. 10A-B) and immunocompromised Ifnar1−/− mice (FIG. 10C-D) blocked the binding between the EDIII WT protein and EDIII-specific neutralizing mAbs more significantly. Since the ZIKV EDIII WT and mutant (M375N/E377T) proteins induced similar titers of total serum IgG antibodies, the above results indicate that the ZIKV EDIII mutant (M375N/E377T) protein induced high-titer serum neutralizing antibodies than the EDIII-WT protein in mice. Therefore, masking the immunodominant non-neutralizing epitope-375 (i.e., NII is negative and has a relatively large absolute value) triggered the host immune system to refocus on less immunodominant but neutralizing epitopes (i.e., NIIs are positive and have relatively small absolute values), accounting for the production of more neutralizing antibodies.

Example 5—Construction, Expression, Immunogenicity, and Efficacy of Other Recombinant ZIKV EDIII Mutant Proteins Materials and Methods Expression and purification of recombinant ZIKV EDIII mutant proteins. This was performed as described above.

Briefly, mutant ZIKV EDIII proteins containing a glycan probe surrounding residue 309 (i.e., T309N/A311T) (SEQ ID NO:13), residue 315 (i.e., T315N/I317T) (SEQ ID NO:14), residue 333 (i.e., A333N) (SEQ ID NO:9), residue 351 (i.e., T351N) (SEQ ID NO:15), residue 366 (i.e., T366N/S368T) (SEQ ID NO:10), residue 369 (i.e., T369N/N371T) (SEQ ID NO:16) and residue 393 (i.e., E393N/K395T) (SEQ ID NO:17) were constructed by multi-site mutagenesis kits using the above ZIKV EDIII wild-type (WT) plasmid fused with a C-terminal human Fc tag as the template. The recombinant proteins were expressed in 293T cell culture supernatants, and purified by Protein A affinity chromatography, as described above.

Animal immunization. The above purified ZIKV EDIII mutant proteins (SEQ ID NO:11-12 and 18-22) were i.m. injected into female BALB/c (4-6-week-old) or male/female Ifnar1−/− (4-6-week old) mice (10 μg/mouse) in the presence of aluminum (500 μg/mouse) and MPL (10 μg/mouse) adjuvant combination. ZIKV EDIII WT protein and PBS were included as controls. The immunized mice were boosted at four weeks, and sera were collected 10 days post-last dose to detect neutralizing antibodies. The immunized mice were subsequently used for the following experiments, including ZIKV challenge and protection evaluation.

ZIKV plaque reduction neutralization test (PRNT). This assay was performed as described above to measure neutralizing antibody titers of immunized mouse sera. Briefly, recent ZIKV human strains PAN2016 or R103451 (100 PFU) were incubated with 2-fold serially diluted mouse sera for 1.5 h at 37° C., which were then added to Vero E6 cells and incubated for 1 h at 37° C. The cells were further overlaid with DMEM containing 1% carboxymethyl cellulose and 2% FBS, and cultured for 4-5 days at 37° C., followed by staining with 0.5% crystal violet, and plaques counted. $PRNT_{50}$ was calculated at 50% plaque reduction using the CalcuSyn computer program, as described above.

ZIKV challenge and evaluation of protection against ZIKV infection. These experiments were carried out as described above. Briefly, ten days post-last dose, the immunized female BALB/c mice were mated with naïve male BALB/c mice. The pregnant BALB/c mice (E10-E13) were pretreated with anti-Ifnar1 blocking antibody (2 mg/mouse) (to become susceptible to ZIKV infection); 24 hours later, the mice were i.p. challenged with ZIKV (strain PAN2016, 5×10$^4$ PFU). ZIKV titers in sera (collected at 3 days p.i.), placenta, fetal brain and amniotic fluid (collected at 5 days p.i.) were detected using plaque-forming assay. The ZIKV titers were detected in Vero E6 cells using around 40 μl of sera/amniotic fluid or 40 mg of tissue samples, so the detection limit was about 25 PFU/ml (for sera and amniotic fluid) or 25 PFU/g of tissue (for placenta and fetal brain).

In a separate experiment, immunized male/female Ifnar1$^{−/−}$ mice were i.p. challenged with ZIKV (strain R103451, 10$^3$ PFU) 13 days post-last dose, and evaluated for survival and weight for 14 days p.i. Mice losing ≥25% body weight were humanely euthanized.

Results

Identification of Other Epitopes (i.e., Residues 333 and 366) on ZIKV EDIII with Significantly Improved Neutralizing Activity and Enhanced Protection of BALB/c Mice and their Fetuses Similar to epitope-375 (i.e., M375N/E377T mutant) described above, we identified several other epitopes (including 309, 315, 333, 351, 366, 369, and 393) on the ZIKV EDIII wild-type (WT) protein, and engineered a N-linked glycan probe onto each of these epitopes to generate single mutations (i.e., A333N and T351N), or double mutations (T309N/A311T, T315N/I317T, T366N/S368T, T369N/N371T, and E393N/K395T), which formed seven N-linked glycosylation sites (SEQ ID NO:9-10 and 13-17). An exemplary structure-based design of ZIKV EDIII mutant (A333N and T366N/S368T) protein vaccines with enhanced efficacy is depicted in FIG. 11. Crystal structure of ZIKV E protein dimer (PDB ID: 5LBV) is depicted in FIG. 11A. The two monomeric subunits (monomer A and B) are on top and bottom, respectively. EDIII of monomeric subunit A is shown on left bottom, and the four residues with increased (A333 and T366) or decreased (T309 and E393) immunogenicity are shown in sticks. Crystal structures of ZIKV EDIII (shown at bottom) complexed with ZIKV EDIII-specific mAbs are depicted in FIG. 11B. Neutralizing mAb ZV-67 (PDB ID: 5KVG) and nonneutralizing mAb ZV-2 (PDB ID: 5KVD) are shown on left and right, respectively. FIG. 11C depicts the introduction of an N-linked glycosylation site to residues T309, A333, T366, and E393 of ZIKV EDIII (after introducing single or double mutations T309N/A311T, A333N, T366N/S368T, and E393N/K395T to EDIII).

We expressed and purified these proteins from 293T cell culture supernatants, and used the mutant, as well as WT (as a control), EDIII proteins to immunize BALB/c mice. We then measured the serum neutralizing antibodies against ZIKV (strain PAN2016), based on which to calculate neutralizing immunogenicity index (NII). The results showed that compared to the EDIII WT, A333N (SEQ ID NO:11) and T366N/S368T (SEQ ID NO: 12) mutant EDIII proteins induced significantly high-titer neutralizing antibodies, whereas T309N/A311T (SEQ ID NO:18) and E393N/K395T (SEQ ID NO:22) mutant EDIII proteins elicited significantly reduced neutralizing antibodies (FIG. 12A). We further calculated the NII values for each of these epitopes on EDIII (using formula: $PRNT_{50\text{-}WT}$-$PRNT_{50\text{-}mutant}$)/$PRNT_{50\text{-}WT}$*100). The results revealed that epitope-333 and epitope-366 had negative values (FIG. 11B), suggesting that these epitopes made negative contributions to the overall neutralizing immunogenicity of ZIKV EDIII vaccine, thus masking them significantly improved vaccine's neutralizing activity. The results also showed that other epitopes, particularly epitope-309 and epitope-393, had positive values (FIG. 12B), suggesting that these epitopes made positive contributions to the overall neutralizing immunogenicity of ZIKV EDIII vaccine, therefore masking them significantly reduced vaccine's neutralizing activity.

We further investigated the efficacy of these mutant ZIKV EDIII protein vaccines in protecting pregnant BALB/c mice and their fetuses against high-dose ZIKV infection. To this end, the above ZIKV WT and mutant EDIII-immunized female BALB/c mice were mated with naïve male BALB/ mice after last-dose, and the pregnant mice were then challenged with ZIKV (strain PAN2016, 5×10$^4$ PFU), followed by detection of viral titers in adult mouse sera (3 days after challenge), placenta, amniotic fluid, and fetal brain (5 days after challenge) by plaque assay. The results indicated that compared to the EDIII-WT-protein-immunized mice, the mutant-EDIII (A333N and T366N/S368T)-immunized mice had significantly reduced viral titers in their sera, placenta, and amniotic fluid (FIG. 12C-E), or undetectable viral titers in the fetal brain (FIG. 12F). In contrast, while the T309N/A311T (SEQ ID NO: 18) and T351N (SEQ ID NO:20)-immunized mice had significantly increased viral titers in their sera (FIG. 12C), the E393N/K395T (SEQ ID NO:22)-immunized mice had significantly increased viral titers in all samples tested, including sera, placenta, amniotic fluid, and fetal brain (FIG. 12C-F). Moreover, the control PBS-treated mice also had significantly higher viral titers in all above samples (FIG. 12C-F). Therefore, compared to the ZIKV EDIII WT protein, the A333N (SEQ ID NO:11) and T366N/S368T (SEQ ID NO:12) mutant EDIII proteins had more potent efficacy in protecting immunocompetent pregnant BALB/c mice and their fetuses against high-dose ZIKV challenge.

Enhanced Neutralizing Activity and Efficacy of ZIKV EDIII Mutant (A333N and T366N/S368T) Proteins in Protecting Immunocompromised Mice Against ZIKV Infection We further evaluated the neutralizing immunogenicity and efficacy of the identified A333N and T366N/S368T, as well as other mutant, ZIKV EDIII protein vaccines in protecting ZIKV-susceptible immunocompromised Ifnar1$^{-/-}$ mice. To this end, we immunized Ifnar1$^{-/-}$ mice with each of the ZIKV mutant, or WT (as a control), EDIII proteins, collected sera to detect neutralizing antibodies and calculate NII values as described above, and then challenged the mice with a ZIKV strain (R103451, 10$^3$ PFU) different from that tested in BABL/c mice 13 days post-last dose, followed by investigation of their survival and weight changes.

The results from neutralization assay showed that compared to the ZIKV EDIII WT, the mutant A333N (SEQ ID NO:11) and T366N/S368T (SEQ ID NO: 12) EDIII proteins elicited significantly high-titer neutralizing antibodies against the above ZIKV strain (FIG. 13A), and that the NII values for epitope-333 and epitope-366 were negative in Ifnar14 mice (FIG. 13B). In contrast, the T315N/1317T (SEQ ID NO:19), T309N/A311T (SEQ ID NO:18), and E393N/K395T (SEQ ID NO:22) mutant EDIII proteins induced reduced, or significantly reduced, neutralizing antibody titers (FIG. 13A), and thus the NII values corresponding to the epitope-315, epitope-309, and epitope-393 were positive (FIG. 13B). The above results were generally consistent with those from the immunized BALB/c mice, further confirming that the contribution of epitope-333 and epitope-366 to the overall neutralizing immunogenicity of the ZIKV EDIII vaccine is negative, and thus masking them significantly improved the vaccine's neutralizing immunogenicity.

The results from challenge study revealed that similar to the EDIII WT-immunized mice, the A333N and T366N/S368T-immunized mice exhibited slightly reduced weight after ZIKV challenge and then increased consistently afterwards (FIG. 13C). Importantly, all mice immunized with either A333N (SEQ ID NO:11) or T366N/S368T (SEQ ID NO: 12) mutant EDIII proteins survived, but only about 58% of the mice immunized with EDIII WT protein survived, at 14 days post-challenge (FIG. 13D), confirming the enhanced efficacy of above two mutant ZIKV EDIII proteins in protecting immunocompromised Ifnar1−/− mice from ZIKV infection. Compared to the EDIII WT-immunized mice, more mice died in the groups immunized with T309N/A311T (SEQ ID NO:18), T315N/1317T (SEQ ID NO:19), and E393N/K395T (SEQ ID NO:22), with survival rates about 50%, 33%, and 17%, respectively, at 14 days after ZIKV challenge (FIG. 13D), indicating the reduced protection of these mutant EDIII proteins with positive NII values. In contrast, mice in the PBS control group exhibited continuously reduced weight, all of which were humanely sacrificed at day 10 after challenge (FIG. 13C-D).

Overall, the protection results from mice immunized with each mutant or WT ZIKV EDIII protein are consistent with respective serum neutralizing antibody titers, suggesting that EDIII vaccine-induced neutralizing antibodies play an important role in preventing ZIKV infection. This line of experimentation further identified A333N and T366N/S368T mutant ZIKV EDIII proteins as novel subunit vaccines against infection of divergent ZIKV strains.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for preventing and/or treating a Zika viral infection in a subject in need thereof, the method comprising:
   administering a therapeutically effective amount of an isolated polypeptide comprising an altered structural envelope (E) protein domain III (EDIII);
   wherein the isolated polypeptide comprises any of SEQ ID NOs 4-6 or 8-22, or a combination thereof; and
   wherein the alteration reduces or prevents the immunogenicity of one or more interfering epitopes of the EDIII.

2. The method of claim 1 further comprising co-administration of an adjuvant.

3. The method of claim 1, wherein the interfering epitope surrounds residue 333, 366, or 375 of ZIKV EDIII polypetide.

4. The method of claim 1, wherein the alteration comprises creation of a site for N-linked glycosylation.

5. The method of claim 4, wherein the alteration comprises at least an N at residue 375 and either a T or S at residue 377.

6. The method of claim 4, wherein the alteration comprises at least an N at residue 333 and either a T or S at residue 335.

7. The method of claim 4, wherein the alteration comprises at least an N at residue 366 and either a T or S at residue 368.

8. The method of claim 5, wherein the alteration comprises M375N/E377T.

9. The method of claim 6, wherein the alteration comprises A333N.

10. The method of claim 7, wherein the alteration comprises T366N/S368T.

11. The method of claim 1, wherein the administration decreases viral titer levels, or viral RNA copy number.

12. The method of claim 1, wherein the administration increases production of neutralizing antibodies.

13. A method for preventing and/or treating a Zika virus infection in a subject in need thereof, the method comprising administering a therapeutically effective amount of an immunogenic composition comprising an isolated polypeptide comprising any of SEQ ID NOs 4-6 or 8-22, or a combination thereof to a subject in need thereof.

14. The method of claim 13, wherein the subject is a woman who is pregnant, who may become pregnant, or who plans to become pregnant.

15. The method of claim 13, wherein the administration increases production of neutralizing antibodies.

16. The method of claim 13, wherein the administration decreases viral titer levels, or viral RNA copy number.

17. The method of claim 14, wherein as a result of the administration, any pregnancy in the woman does not result in Zika virus-associated birth defects.

* * * * *

SEQUENCE LISTING

```
<160> NUMBER OF SEQ ID NOS: 27

<210> SEQ ID NO 1
<211> LENGTH: 676
<212> TYPE: PRT
<213> ORGANISM: Zika Virus

<400> SEQUENCE: 1

Val Thr Arg Arg Gly Ser Ala Tyr Tyr Met Tyr Leu Asp Arg Asn Asp
1               5                   10                  15

Ala Gly Glu Ala Ile Ser Phe Pro Thr Thr Leu Gly Met Asn Lys Cys
            20                  25                  30

Tyr Ile Gln Ile Met Asp Leu Gly His Met Cys Asp Ala Thr Met Ser
        35                  40                  45

Tyr Glu Cys Pro Met Leu Asp Glu Gly Val Glu Pro Asp Asp Val Asp
    50                  55                  60

Cys Trp Cys Asn Thr Thr Ser Thr Trp Val Val Tyr Gly Thr Cys His
65                  70                  75                  80

His Lys Lys Gly Glu Ala Arg Arg Ser Arg Arg Ala Val Thr Leu Pro
                85                  90                  95

Ser His Ser Thr Arg Lys Leu Gln Thr Arg Ser Gln Thr Trp Leu Glu
            100                 105                 110

Ser Arg Glu Tyr Thr Lys His Leu Ile Arg Val Glu Asn Trp Ile Phe
        115                 120                 125

Arg Asn Pro Gly Phe Ala Leu Ala Ala Ala Ile Ala Trp Leu Leu
    130                 135                 140

Gly Ser Ser Thr Ser Gln Lys Val Ile Tyr Leu Val Met Ile Leu Leu
145                 150                 155                 160

Ile Ala Pro Ala Tyr Ser Ile Arg Cys Ile Gly Val Ser Asn Arg Asp
                165                 170                 175

Phe Val Glu Gly Met Ser Gly Gly Thr Trp Val Asp Ile Val Leu Glu
            180                 185                 190

His Gly Gly Cys Val Thr Val Met Ala Gln Asp Lys Pro Thr Val Asp
        195                 200                 205

Ile Glu Leu Val Thr Thr Thr Val Ser Asn Met Ala Glu Val Arg Ser
    210                 215                 220

Tyr Cys Tyr Glu Ala Ser Ile Ser Asp Met Ala Ser Asp Ser Arg Cys
225                 230                 235                 240

Pro Thr Gln Gly Glu Ala Tyr Leu Asp Lys Gln Ser Asp Thr Gln Tyr
                245                 250                 255

Val Cys Lys Arg Thr Leu Val Asp Arg Gly Trp Gly Asn Gly Cys Gly
```

```
            260                 265                 270
Leu Phe Gly Lys Gly Ser Leu Val Thr Cys Ala Lys Phe Ala Cys Ser
            275                 280                 285

Lys Lys Met Thr Gly Lys Ser Ile Gln Pro Glu Asn Leu Glu Tyr Arg
290                 295                 300

Ile Met Leu Ser Val His Gly Ser Gln His Ser Gly Met Ile Val Asn
305                 310                 315                 320

Asp Thr Gly His Glu Thr Asp Glu Asn Arg Ala Lys Val Glu Ile Thr
            325                 330                 335

Pro Asn Ser Pro Arg Ala Glu Ala Thr Leu Gly Gly Phe Gly Ser Leu
            340                 345                 350

Gly Leu Asp Cys Glu Pro Arg Thr Gly Leu Asp Phe Ser Asp Leu Tyr
            355                 360                 365

Tyr Leu Thr Met Asn Asn Lys His Trp Leu Val His Lys Glu Trp Phe
            370                 375                 380

His Asp Ile Pro Leu Pro Trp His Ala Gly Ala Asp Thr Gly Thr Pro
385                 390                 395                 400

His Trp Asn Asn Lys Glu Ala Leu Val Glu Phe Lys Asp Ala His Ala
            405                 410                 415

Lys Arg Gln Thr Val Val Val Leu Gly Ser Gln Glu Gly Ala Val His
            420                 425                 430

Thr Ala Leu Ala Gly Ala Leu Glu Ala Glu Met Asp Gly Ala Lys Gly
            435                 440                 445

Arg Leu Ser Ser Gly His Leu Lys Cys Arg Leu Lys Met Asp Lys Leu
450                 455                 460

Arg Leu Lys Gly Val Ser Tyr Ser Leu Cys Thr Ala Ala Phe Thr Phe
465                 470                 475                 480

Thr Lys Ile Pro Ala Glu Thr Leu His Gly Thr Val Thr Val Glu Val
            485                 490                 495

Gln Tyr Ala Gly Thr Asp Gly Pro Cys Lys Val Pro Ala Gln Met Ala
            500                 505                 510

Val Asp Met Gln Thr Leu Thr Pro Val Gly Arg Leu Ile Thr Ala Asn
            515                 520                 525

Pro Val Ile Thr Glu Ser Thr Glu Asn Ser Lys Met Met Leu Glu Leu
530                 535                 540

Asp Pro Pro Phe Gly Asp Ser Tyr Ile Val Ile Gly Val Gly Glu Lys
545                 550                 555                 560

Lys Ile Thr His His Trp His Arg Ser Gly Ser Thr Ile Gly Lys Ala
            565                 570                 575

Phe Glu Ala Thr Val Arg Gly Ala Lys Arg Met Ala Val Leu Gly Asp
            580                 585                 590

Thr Ala Trp Asp Phe Gly Ser Val Gly Gly Ala Leu Asn Ser Leu Gly
            595                 600                 605

Lys Gly Ile His Gln Ile Phe Gly Ala Ala Phe Lys Ser Leu Phe Gly
            610                 615                 620

Gly Met Ser Trp Phe Ser Gln Ile Leu Ile Gly Thr Leu Leu Met Trp
625                 630                 635                 640

Leu Gly Leu Asn Thr Lys Asn Gly Ser Ile Ser Leu Met Cys Leu Ala
            645                 650                 655

Leu Gly Gly Val Leu Ile Phe Leu Ser Thr Ala Val Ser Ala Asp Val
            660                 665                 670

Gly Cys Ser Val
            675
```

<210> SEQ ID NO 2
<211> LENGTH: 505
<212> TYPE: PRT
<213> ORGANISM: Zika Virus

<400> SEQUENCE: 2

```
Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
```

```
                    370                 375                 380
Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala Asp
                500                 505
```

<210> SEQ ID NO 3
<211> LENGTH: 112
<212> TYPE: PRT
<213> ORGANISM: Zika Virus

<400> SEQUENCE: 3

```
Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110
```

<210> SEQ ID NO 4
<211> LENGTH: 112
<212> TYPE: PRT
<213> ORGANISM: Artificial Sequence
<220> FEATURE:
<223> OTHER INFORMATION: ZIKV EDIII M375N/E377T protein

<400> SEQUENCE: 4

```
Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Asn Leu Thr
65                  70                  75                  80
```

-continued

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

<210> SEQ ID NO 5
<211> LENGTH: 341
<212> TYPE: PRT
<213> ORGANISM: Artificial Sequence
<220> FEATURE:
<223> OTHER INFORMATION: ZIKV EDIII WT-Fc protein

<400> SEQUENCE: 5

Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

Arg Ser Asp Lys Thr His Thr Cys Pro Pro Cys Pro Ala Pro Glu Leu
            115                 120                 125

Leu Gly Gly Pro Ser Val Phe Leu Phe Pro Pro Lys Pro Lys Asp Thr
        130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
        340

<210> SEQ ID NO 6
<211> LENGTH: 341
<212> TYPE: PRT
<213> ORGANISM: Artificial Sequence
<220> FEATURE:
<223> OTHER INFORMATION: ZIKV EDIII M375N/E377T-Fc protein

<400> SEQUENCE: 6

Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Asn Leu Thr
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

Arg Ser Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
        340

<210> SEQ ID NO 7
<211> LENGTH: 118
<212> TYPE: PRT
<213> ORGANISM: Artificial Sequence
<220> FEATURE:
<223> OTHER INFORMATION: ZIKV EDIII WT-His protein

<400> SEQUENCE: 7

```
Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

His His His His His His
        115
```

<210> SEQ ID NO 8
<211> LENGTH: 118
<212> TYPE: PRT
<213> ORGANISM: Artificial Sequence
<220> FEATURE:
<223> OTHER INFORMATION: ZIKV EDIII M375N/E377T-His protein

<400> SEQUENCE: 8

```
Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Asn Leu Thr
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

His His His His His His
        115
```

<210> SEQ ID NO 9
<211> LENGTH: 112
<212> TYPE: PRT
<213> ORGANISM: Artificial Sequence
<220> FEATURE:
<223> OTHER INFORMATION: ZIKV EDIII A333N protein

<400> SEQUENCE: 9

-continued

```
Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Asn Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110
```

<210> SEQ ID NO 10
<211> LENGTH: 112
<212> TYPE: PRT
<213> ORGANISM: Artificial Sequence
<220> FEATURE:
<223> OTHER INFORMATION: ZIKV EDIII T366N/S368T protein

<400> SEQUENCE: 10

```
Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Asn Glu Thr Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110
```

<210> SEQ ID NO 11
<211> LENGTH: 341
<212> TYPE: PRT
<213> ORGANISM: Artificial Sequence
<220> FEATURE:
<223> OTHER INFORMATION: ZIKV EDIII A333N-Fc protein

<400> SEQUENCE: 11

```
Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Asn Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95
```

Lys Lys Ile Thr His His Trp His Arg Ser Gly Ser Thr Ile Gly Lys
            100                 105                 110

Arg Ser Asp Lys Thr His Thr Cys Pro Pro Cys Pro Ala Pro Glu Leu
            115                 120                 125

Leu Gly Gly Pro Ser Val Phe Leu Phe Pro Pro Lys Pro Lys Asp Thr
        130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
        210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
        290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 12
<211> LENGTH: 341
<212> TYPE: PRT
<213> ORGANISM: Artificial Sequence
<220> FEATURE:
<223> OTHER INFORMATION: ZIKV EDIII T366N/S368T-Fc protein

<400> SEQUENCE: 12

Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Asn Glu Thr Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

Arg Ser Asp Lys Thr His Thr Cys Pro Pro Cys Pro Ala Pro Glu Leu
115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 13
<211> LENGTH: 112
<212> TYPE: PRT
<213> ORGANISM: Artificial Sequence
<220> FEATURE:
<223> OTHER INFORMATION: ZIKV EDIII T309N/A311T protein

<400> SEQUENCE: 13

Leu Arg Leu Lys Gly Val Ser Tyr Ser Leu Cys Asn Ala Thr Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

<210> SEQ ID NO 14

-continued

```
<211> LENGTH: 112
<212> TYPE: PRT
<213> ORGANISM: Artificial Sequence
<220> FEATURE:
<223> OTHER INFORMATION: ZIKV EDIII T315N/I317T protein

<400> SEQUENCE: 14

Leu Arg Leu Lys Gly Val Ser Tyr Ser Leu Cys Thr Ala Ala Phe Thr
1               5                   10                  15

Phe Asn Lys Thr Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: ZIKV EDIII T351N protein

<400> SEQUENCE: 15

Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Asn Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: ZIKV EDIII T369N/N371T protein

<400> SEQUENCE: 16

Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45
```

```
Ala Val Asp Met Gln Thr Leu Thr Pro Val Gly Arg Leu Ile Thr Ala
 50                  55                  60

Asn Pro Val Ile Thr Glu Ser Asn Glu Thr Ser Lys Met Met Leu Glu
 65                  70                  75                  80

Leu Asp Pro Pro Phe Gly Asp Ser Tyr Ile Val Ile Gly Val Gly Glu
                 85                  90                  95

Lys Lys Ile Thr His His Trp His Arg Ser Gly Ser Thr Ile Gly Lys
            100                 105                 110
```

<210> SEQ ID NO 17
<211> LENGTH: 112
<212> TYPE: PRT
<213> ORGANISM: Artificial Sequence
<220> FEATURE:
<223> OTHER INFORMATION: ZIKV EDIII E393N/K395T protein

<400> SEQUENCE: 17

```
Leu Arg Leu Lys Gly Val Ser Tyr Ser Leu Cys Thr Ala Ala Phe Thr
 1               5                  10                  15

Phe Thr Lys Ile Pro Ala Glu Thr Leu His Gly Thr Val Thr Val Glu
                 20                  25                  30

Val Gln Tyr Ala Gly Thr Asp Gly Pro Cys Lys Val Pro Ala Gln Met
             35                  40                  45

Ala Val Asp Met Gln Thr Leu Thr Pro Val Gly Arg Leu Ile Thr Ala
 50                  55                  60

Asn Pro Val Ile Thr Glu Ser Thr Glu Asn Ser Lys Met Met Leu Glu
 65                  70                  75                  80

Leu Asp Pro Pro Phe Gly Asp Ser Tyr Ile Val Ile Gly Val Gly Asn
                 85                  90                  95

Lys Thr Ile Thr His His Trp His Arg Ser Gly Ser Thr Ile Gly Lys
            100                 105                 110
```

<210> SEQ ID NO 18
<211> LENGTH: 341
<212> TYPE: PRT
<213> ORGANISM: Artificial Sequence
<220> FEATURE:
<223> OTHER INFORMATION: ZIKV EDIII T309N/A311T-Fc protein

<400> SEQUENCE: 18

```
Leu Arg Leu Lys Gly Val Ser Tyr Ser Leu Cys Asn Ala Thr Phe Thr
 1               5                  10                  15

Phe Thr Lys Ile Pro Ala Glu Thr Leu His Gly Thr Val Thr Val Glu
                 20                  25                  30

Val Gln Tyr Ala Gly Thr Asp Gly Pro Cys Lys Val Pro Ala Gln Met
             35                  40                  45

Ala Val Asp Met Gln Thr Leu Thr Pro Val Gly Arg Leu Ile Thr Ala
 50                  55                  60

Asn Pro Val Ile Thr Glu Ser Thr Glu Asn Ser Lys Met Met Leu Glu
 65                  70                  75                  80

Leu Asp Pro Pro Phe Gly Asp Ser Tyr Ile Val Ile Gly Val Gly Glu
                 85                  90                  95

Lys Lys Ile Thr His His Trp His Arg Ser Gly Ser Thr Ile Gly Lys
            100                 105                 110

Arg Ser Asp Lys Thr His Thr Cys Pro Pro Cys Pro Ala Pro Glu Leu
            115                 120                 125

Leu Gly Gly Pro Ser Val Phe Leu Phe Pro Pro Lys Pro Lys Asp Thr
            130                 135                 140
```

```
Leu Met Ile Ser Arg Thr Pro Glu Val Thr Cys Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 19
<211> LENGTH: 341
<212> TYPE: PRT
<213> ORGANISM: Artificial Sequence
<220> FEATURE:
<223> OTHER INFORMATION: ZIKV EDIII T315N/I317T-Fc protein

<400> SEQUENCE: 19

Leu Arg Leu Lys Gly Val Ser Tyr Ser Leu Cys Thr Ala Ala Phe Thr
1               5                   10                  15

Phe Asn Lys Thr Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

Arg Ser Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160
```

Ser His Glu Asp Pro Glu Val Lys Phe Asn Trp Tyr Val Asp Gly Val
            165                 170                 175

Glu Val His Asn Ala Lys Thr Lys Pro Arg Glu Glu Gln Tyr Asn Ser
        180                 185                 190

Thr Tyr Arg Val Val Ser Val Leu Thr Val Leu His Gln Asp Trp Leu
            195                 200                 205

Asn Gly Lys Glu Tyr Lys Cys Lys Val Ser Asn Lys Ala Leu Pro Ala
        210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
            245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
            275                 280                 285

Pro Pro Val Leu Asp Ser Asp Gly Ser Phe Phe Leu Tyr Ser Lys Leu
        290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
            325                 330                 335

Leu Ser Pro Gly Lys
            340

<210> SEQ ID NO 20
<211> LENGTH: 341
<212> TYPE: PRT
<213> ORGANISM: Artificial Sequence
<220> FEATURE:
<223> OTHER INFORMATION: ZIKV EDIII T351N-Fc protein

<400> SEQUENCE: 20

Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Asn Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Glu
            85                  90                  95

Lys Lys Ile Thr His His Trp His Arg Ser Gly Ser Thr Ile Gly Lys
        100                 105                 110

Arg Ser Asp Lys Thr His Thr Cys Pro Pro Cys Pro Ala Pro Glu Leu
    115                 120                 125

Leu Gly Gly Pro Ser Val Phe Leu Phe Pro Pro Lys Pro Lys Asp Thr
        130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
            165                 170                 175

Glu Val His Asn Ala Lys Thr Lys Pro Arg Glu Glu Gln Tyr Asn Ser
                180                 185                 190

Thr Tyr Arg Val Val Ser Val Leu Thr Val Leu His Gln Asp Trp Leu
            195                 200                 205

Asn Gly Lys Glu Tyr Lys Cys Lys Val Ser Asn Lys Ala Leu Pro Ala
        210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 21
<211> LENGTH: 341
<212> TYPE: PRT
<213> ORGANISM: Artificial Sequence
<220> FEATURE:
<223> OTHER INFORMATION: ZIKV EDIII T369N/N371T-Fc protein

<400> SEQUENCE: 21

Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
                20                  25                  30

Val Gln Tyr Ala Gly Thr Asp Gly Pro Cys Lys Val Pro Ala Gln Met
            35                  40                  45

Ala Val Asp Met Gln Thr Leu Thr Pro Val Gly Arg Leu Ile Thr Ala
        50                  55                  60

Asn Pro Val Ile Thr Glu Ser Asn Glu Thr Ser Lys Met Met Leu Glu
65                  70                  75                  80

Leu Asp Pro Pro Phe Gly Asp Ser Tyr Ile Val Ile Gly Val Gly Glu
                85                  90                  95

Lys Lys Ile Thr His His Trp His Arg Ser Gly Ser Thr Ile Gly Lys
            100                 105                 110

Arg Ser Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

```
Thr Tyr Arg Val Val Ser Val Leu Thr Val Leu His Gln Asp Trp Leu
            195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 22
<211> LENGTH: 341
<212> TYPE: PRT
<213> ORGANISM: Artificial Sequence
<220> FEATURE:
<223> OTHER INFORMATION: ZIKV EDIII E393N/K395T-Fc protein

<400> SEQUENCE: 22

Leu Arg Leu Lys Gly Val Ser Tyr Ser Leu Cys Thr Ala Ala Phe Thr
1               5                   10                  15

Phe Thr Lys Ile Pro Ala Glu Thr Leu His Gly Thr Val Thr Val Glu
            20                  25                  30

Val Gln Tyr Ala Gly Thr Asp Gly Pro Cys Lys Val Pro Ala Gln Met
        35                  40                  45

Ala Val Asp Met Gln Thr Leu Thr Pro Val Gly Arg Leu Ile Thr Ala
    50                  55                  60

Asn Pro Val Ile Thr Glu Ser Thr Glu Asn Ser Lys Met Met Leu Glu
65                  70                  75                  80

Leu Asp Pro Pro Phe Gly Asp Ser Tyr Ile Val Ile Gly Val Gly Asn
                85                  90                  95

Lys Thr Ile Thr His His Trp His Arg Ser Gly Ser Thr Ile Gly Lys
            100                 105                 110

Arg Ser Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205
```

Asn Gly Lys Glu Tyr Lys Cys Lys Val Ser Asn Lys Ala Leu Pro Ala
            210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
            325                 330                 335

Leu Ser Pro Gly Lys
            340

<210> SEQ ID NO 23
<211> LENGTH: 229
<212> TYPE: PRT
<213> ORGANISM: Homo sapiens

<400> SEQUENCE: 23

Arg Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
210                 215                 220

Leu Ser Pro Gly Lys

```
<210> SEQ ID NO 24
<211> LENGTH: 27
<212> TYPE: PRT
<213> ORGANISM: Artificial Sequence
<220> FEATURE:
<223> OTHER INFORMATION: Foldon

<400> SEQUENCE: 24

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 25
<211> LENGTH: 32
<212> TYPE: PRT
<213> ORGANISM: Artificial Sequence
<220> FEATURE:
<223> OTHER INFORMATION: GCN4 trimerization motif

<400> SEQUENCE: 25

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30

<210> SEQ ID NO 26
<211> LENGTH: 23
<212> TYPE: DNA
<213> ORGANISM: Artificial Sequence
<220> FEATURE:
<223> OTHER INFORMATION: ZIKV forward primer

<400> SEQUENCE: 26
ttggtcatga tactgctgat tgc                                     23

<210> SEQ ID NO 27
<211> LENGTH: 22
<212> TYPE: DNA
<213> ORGANISM: Artificial Sequence
<220> FEATURE:
<223> OTHER INFORMATION: ZIKV reverse primer

<400> SEQUENCE: 27
ccttccacaa agtccctatt gc                                      22
```

UNITED STATES PATENT AND TRADEMARK OFFICE
CERTIFICATE OF CORRECTION

| | | |
|---|---|---|
| PATENT NO. | : 12,064,476 B2 | Page 1 of 1 |
| APPLICATION NO. | : 17/287938 | |
| DATED | : August 20, 2024 | |
| INVENTOR(S) | : Lanying Du, Wanbo Tai and Fang Li | |

It is certified that error appears in the above-identified patent and that said Letters Patent is hereby corrected as shown below:

In the Specification

In Column 1, Line 18, delete "R01AI139092 and R21AI137790" and insert -- AI139092 and AI137790 --

In Column 1, Line 19-21, delete "and Grant No. NYB475, Grant No. NYB486, and Grant No. NYB552 awarded by the New York Blood Center"

Signed and Sealed this
Eighth Day of July, 2025

Coke Morgan Stewart
*Acting Director of the United States Patent and Trademark Office*